US009339639B2

(12) United States Patent
Halili et al.

(10) Patent No.: US 9,339,639 B2
(45) Date of Patent: May 17, 2016

(54) SEALING ASSEMBLY FOR A FLUID RESERVOIR OF A FLUID INFUSION DEVICE

(75) Inventors: Edgardo C. Halili, Santa Clarita, CA (US); Eric M. Lorenzen, Granada Hills, CA (US); Matthew William Yavorsky, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 268 days.

(21) Appl. No.: 13/399,857

(22) Filed: Feb. 17, 2012

(65) Prior Publication Data

US 2012/0211947 A1    Aug. 23, 2012

Related U.S. Application Data

(60) Provisional application No. 61/445,393, filed on Feb. 22, 2011.

(51) Int. Cl.
*A61M 37/00* (2006.01)
*A61M 39/00* (2006.01)
(Continued)

(52) U.S. Cl.
CPC .............. *A61M 39/00* (2013.01); *A61M 5/142* (2013.01); *A61M 5/1452* (2013.01);
(Continued)

(58) Field of Classification Search
CPC ... A61M 5/14; A61M 5/142; A61M 5/14566; A61M 16/20; A61M 39/0208; A61M 39/04; A61M 39/045; A61M 39/06; A61M 39/0606; A61M 39/0693; A61M 39/14; A61M 39/22; A61M 39/221; A61M 39/24; A61M 39/26; A61M 2039/027; A61M 2039/04; A61M 5/14244; A61M 5/14248; A61M 5/145; A61M 5/1452; A61M 5/1456; A61M 5/162; A61M 2005/14268; A61M 2005/14573; A61M 5/16881; A61M 2005/14252; A61M 2005/1623; A61M 2005/3123; A61M 39/00; A61M 39/10; A61M 39/12; A61M 2039/0072; A61M 2039/0081; A61M 2039/1066; A61M 2039/248; A61M 2039/266; A61M 2039/267; A61M 2202/0468; A61M 2202/07; A61M 5/31
USPC .............. 604/93.01, 167.03, 288.01, 288.02, 604/288.03
See application file for complete search history.

(56) References Cited

U.S. PATENT DOCUMENTS 3,631,847 A   1/1972  Hobbs, II
4,212,738 A   7/1980  Henne
(Continued)

FOREIGN PATENT DOCUMENTS

DE   4329229   3/1995
EP   0319268   11/1988
(Continued)

OTHER PUBLICATIONS

PCT Search Report (PCT/US02/03299), Oct. 31, 2002, Medtronic Minimed, Inc.
(Continued)

*Primary Examiner* — Edelmira Bosques
*Assistant Examiner* — Nicholas Meghri
(74) *Attorney, Agent, or Firm* — Ingrassia Fisher & Lorenz, P.C.

(57) ABSTRACT

Disclosed herein is a fluid infusion device of the type that delivers medication fluid to the body of a patient. The device includes or cooperates with a fluid reservoir, and the device has a sealing assembly to receive and form a fluid seal with the fluid reservoir. A retractable sealing element surrounding a hollow fluid delivery needle may be used to seal a port of the fluid reservoir. The port may include a pressure vent that is sealed by the retractable sealing element. In one variation, the reservoir includes a moving valve sleeve that holds a septum. The septum moves to allow the reservoir to vent, and to form a seal with the port when the needle pierces the septum. In another variation, the device includes a needleless sealing assembly. In yet other variations, the device uses a needled fluid reservoir.

21 Claims, 19 Drawing Sheets

(51) Int. Cl.
  *A61M 5/142* (2006.01)
  *A61M 5/145* (2006.01)
  *A61M 5/162* (2006.01)
  *A61M 5/168* (2006.01)
  *A61M 5/31* (2006.01)
  *A61M 39/10* (2006.01)
  *A61M 39/12* (2006.01)
  *A61M 39/24* (2006.01)
  *A61M 39/26* (2006.01)

(52) U.S. Cl.
  CPC .......... *A61M 5/14248* (2013.01); *A61M 5/162* (2013.01); *A61M 5/16881* (2013.01); *A61M 5/31* (2013.01); *A61M 39/10* (2013.01); *A61M 39/12* (2013.01); *A61M 2005/14252* (2013.01); *A61M 2005/1623* (2013.01); *A61M 2005/3123* (2013.01); *A61M 2039/0072* (2013.01); *A61M 2039/0081* (2013.01); *A61M 2039/1066* (2013.01); *A61M 2039/248* (2013.01); *A61M 2039/266* (2013.01); *A61M 2039/267* (2013.01); *A61M 2202/0468* (2013.01); *A61M 2202/07* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,512,766 A | 4/1985 | Vailancourt |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,520,665 A | 5/1996 | Fleetwood |
| 5,543,326 A | 8/1996 | Heller et al. |
| 5,549,566 A * | 8/1996 | Elias et al. ............... 604/167.03 |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,840,063 A | 11/1998 | Flaherty |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |

(56) References Cited

U.S. PATENT DOCUMENTS

| | | |
|---|---|---|
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Llamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Llamos et al. |
| 7,153,263 B2 | 12/2006 | Carter et al. |
| 7,153,289 B2 | 12/2006 | Vasko |
| 7,396,330 B2 | 7/2008 | Banet et al. |
| 7,828,764 B2 | 11/2010 | Moberg et al. |
| 7,905,868 B2 | 3/2011 | Moberg et al. |
| 7,981,076 B2 | 7/2011 | Sullivan et al. |
| 8,105,314 B2 | 1/2012 | Fangrow, Jr. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0087715 A1 | 4/2005 | Doyle |
| 2005/0101932 A1* | 5/2005 | Cote et al. ............ 604/506 |
| 2005/0154271 A1 | 7/2005 | Rasdal et al. |
| 2005/0165365 A1 | 7/2005 | Newton et al. |
| 2005/0192557 A1 | 9/2005 | Brauker et al. |
| 2006/0211990 A1* | 9/2006 | Fangrow, Jr. ............ 604/157 |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0083162 A1 | 4/2007 | O'Reagan et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2008/0269687 A1 | 10/2008 | Chong et al. |
| 2009/0081951 A1 | 3/2009 | Erdmann et al. |
| 2009/0082635 A1 | 3/2009 | Baldus et al. |
| 2009/0204077 A1 | 8/2009 | Hasted et al. |
| 2009/0254041 A1* | 10/2009 | Krag et al. ............ 604/180 |
| 2009/0299290 A1 | 12/2009 | Moberg |
| 2011/0036844 A1 | 2/2011 | Gyrn et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 93/11828 A1 | 6/1993 |
| WO | WO 96/13301 A2 | 5/1996 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/20070 A1 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

(56) References Cited

FOREIGN PATENT DOCUMENTS

| WO | WO 2008/064092 A2 | 5/2008 |
|---|---|---|
| WO | WO2009/102355 A2 | 8/2009 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-Tron® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.

(56) References Cited

OTHER PUBLICATIONS

Mastrototaro, John J., et al., "An electroenzymatic glucose sensor fabricated on a flexible substrate," Sensors & Actuators, B. 5, 1991, pp. 139-144.

Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

PCT Invitation & Partial Search for PCT/US2012/025825, Jun. 21, 2012, Medtronic Minimed, Inc.

* cited by examiner

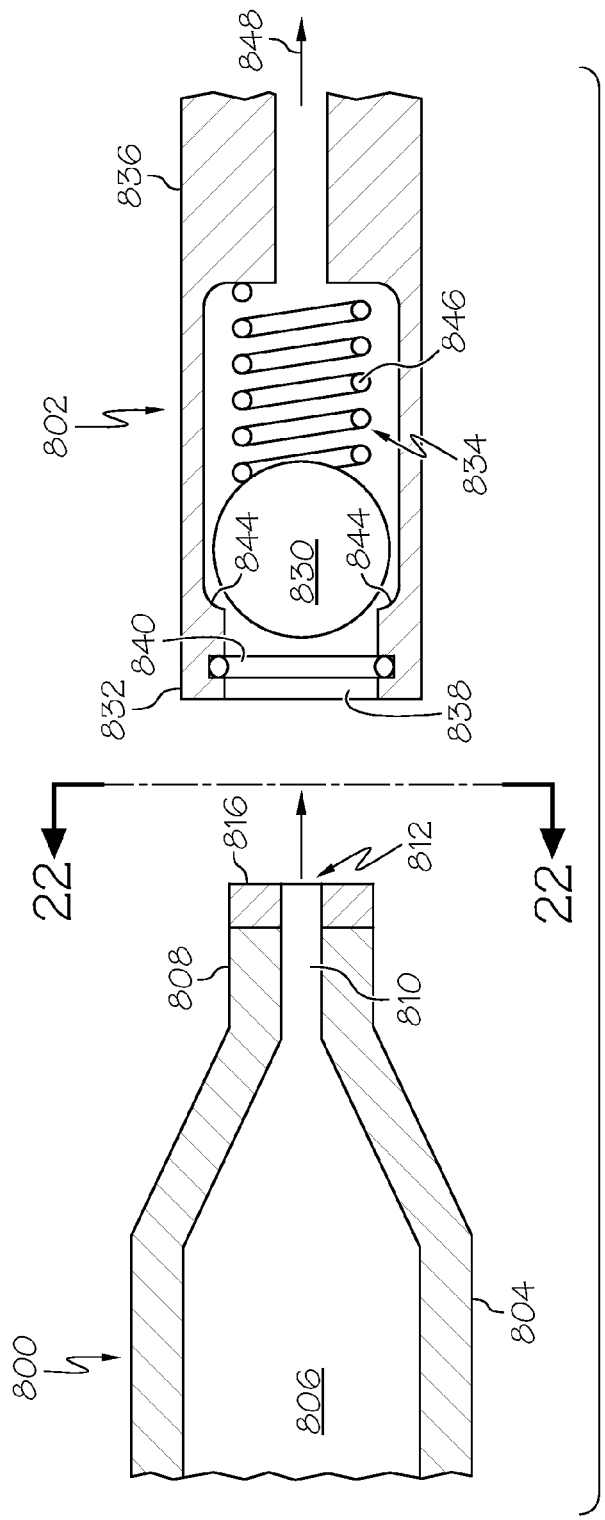
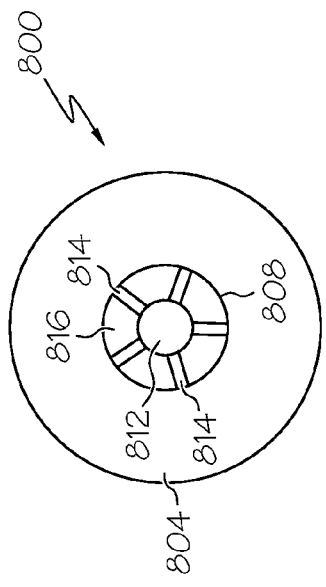
FIG. 21
FIG. 22

SEALING ASSEMBLY FOR A FLUID RESERVOIR OF A FLUID INFUSION DEVICE

CROSS-REFERENCE TO RELATED APPLICATION

This application claims the benefit of U.S. provisional patent application Ser. No. 61/445,393, filed Feb. 22, 2011 (the entire content of which is incorporated by reference herein).

TECHNICAL FIELD

Embodiments of the subject matter described herein relate generally to fluid infusion devices for delivering a medication fluid to the body of a user. More particularly, embodiments of the subject matter relate to a sealing element that provides a fluid seal between a fluid delivery needle and a removable fluid reservoir.

BACKGROUND

Certain diseases or conditions may be treated, according to modern medical techniques, by delivering a medication or other substance to the body of a patient, either in a continuous manner or at particular times or time intervals within an overall time period. For example, diabetes is commonly treated by delivering defined amounts of insulin to the patient at appropriate times. Some common modes of providing insulin therapy to a patient include delivery of insulin through manually operated syringes and insulin pens. Other modern systems employ programmable fluid infusion devices (e.g., insulin pumps) to deliver controlled amounts of insulin to a patient.

A fluid infusion device suitable for use as an insulin pump may be realized as an external device or an implantable device, which is surgically implanted into the body of the patient. External fluid infusion devices include devices designed for use in a generally stationary location (for example, in a hospital or clinic), and devices configured for ambulatory or portable use (to be carried by a patient). External fluid infusion devices may establish a fluid flow path from a fluid reservoir to the patient via, for example, a suitable hollow tubing. The hollow tubing may be connected to a hollow fluid delivery needle that is designed to pierce the patient's skin to deliver an infusion medium to the body. Alternatively, the hollow tubing may be connected directly to the patient's body through a cannula or set of micro-needles.

The fluid reservoir of an external fluid infusion device may be realized as a single-use prefilled disposable unit, a patient-filled unit, a refillable unit, or the like. The fluid reservoir for a typical fluid infusion device is implemented as a removable and replaceable component. To this end, the fluid infusion device includes structure, features, and/or elements that are designed to establish the fluid flow path with the fluid reservoir. For example, a fluid seal between the fluid reservoir and a hollow fluid delivery needle may be established when the fluid reservoir is properly installed in the fluid infusion device. When the fluid reservoir is removed (for purposes of replacement, to allow certain activities such as swimming or bathing, or the like), the fluid delivery needle should be protected against contamination.

Accordingly, it is desirable to implement a sealing element that creates a seal between a removable fluid reservoir and a delivery needle of a fluid infusion device. Furthermore, other desirable features and characteristics will become apparent from the subsequent detailed description and the appended claims, taken in conjunction with the accompanying drawings and the foregoing technical field and background.

BRIEF SUMMARY

Various embodiments of a fluid infusion device, along with related fluid reservoirs and sealing elements for fluid reservoirs, are provided here. For example, an embodiment of a sealing element for a fluid infusion device is provided. The sealing element includes a base section, a tip section extending from the base section, a retractable body section between the base section and the tip section, and a needle cavity formed in the retractable body section. The needle cavity continues through the base section to define a needle opening in the base section, and the needle cavity is sized to receive the hollow fluid delivery needle. The sealing element also includes a self-sealing slit formed in the tip section to accommodate the hollow fluid delivery needle when the sealing element is in a retracted position.

Another embodiment of a sealing element for a fluid infusion device is also provided. The sealing element includes a base section, a tip section extending from the base section, a retractable body section between the base section and the tip section, and a needle cavity formed in the retractable body section and continuing through the base section to define a needle opening in the base section. The needle cavity is sized to receive the hollow fluid delivery needle, and the needle cavity defines internal relief features of the retractable body section. The internal relief features cause the sealing element to deform and retract over the hollow fluid delivery needle in response to a longitudinal force applied to the tip section. In addition, the internal relief features cause the sealing element to regain a nominal shape, extend over the hollow fluid delivery needle, and enclose the hollow fluid delivery needle in response to removal of the longitudinal force.

An embodiment of a sealing assembly for a fluid infusion device is also provided. The fluid infusion device cooperates with a fluid reservoir having a fluid delivery port. The sealing assembly includes a base plate, a hollow fluid delivery needle coupled to the base plate to provide a fluid flow path from the fluid reservoir to a user of the fluid infusion device, and a sealing element coupled to the base plate and overlying at least a portion of the hollow fluid delivery needle. The sealing element includes a base section, a tip section extending from the base section, a retractable body section between the base section and the tip section, a needle cavity formed in the retractable body section and continuing through the base section to define a needle opening in the base section, and a self-sealing slit formed in the tip section. The needle cavity is sized to receive the hollow fluid delivery needle, and the self-sealing slit accommodates the hollow fluid delivery needle when the sealing element is in a retracted position.

Another embodiment of a sealing assembly for a fluid infusion device is also provided. The sealing assembly includes a base plate, a hollow fluid delivery needle coupled to the base plate to provide a fluid flow path from the fluid reservoir to a user of the fluid infusion device, and a sealing element coupled to the base plate and overlying at least a portion of the hollow fluid delivery needle. The sealing element includes a base section, a tip section extending from the base section, a retractable body section between the base section and the tip section, and a needle cavity formed in the retractable body section and continuing through the base section to define a needle opening in the base section. The needle cavity is sized to receive the hollow fluid delivery needle, and the needle cavity defines internal relief features of the retractable body section. The internal relief features promote deformation of the sealing element and retraction of the sealing element over the hollow fluid delivery needle in response to a longitudinal force applied to the tip section of the sealing element. Moreover, the internal relief features cause the sealing element to automatically extend over the hollow fluid delivery needle into a nominal state in response to removal of the longitudinal force.

Also presented here is an embodiment of a fluid infusion device to deliver a fluid to a user. The fluid infusion device includes a base plate, a hollow fluid delivery needle coupled to the base plate to provide a fluid flow path from the fluid infusion device to the user, and a sealing element coupled to the base plate and overlying at least a portion of the hollow fluid delivery needle. The sealing element includes a base section, a tip section extending from the base section, a retractable body section between the base section and the tip section, a needle cavity formed in the retractable body section and continuing through the base section to define a needle opening in the base section, the needle cavity sized to receive the hollow fluid delivery needle, and a self-sealing slit formed in the tip section. The fluid infusion device also includes a removable fluid reservoir having a fluid delivery port to receive a tip of the hollow fluid delivery needle. When the removable fluid reservoir is removed from the hollow fluid delivery needle, the retractable body section extends such that the hollow fluid delivery needle is enclosed by the sealing element and such that the self-sealing slit forms a fluid seal to inhibit fluid ingress into the needle cavity. When the removable fluid reservoir is installed on the hollow fluid delivery needle, the tip of the hollow fluid delivery needle extends from the tip section and into the fluid reservoir, and the retractable body section deforms to create a radial seal with an interior of the fluid delivery port.

Another embodiment of a fluid infusion device is also presented here. The fluid infusion device includes a base plate, a hollow fluid delivery needle coupled to the base plate to provide a fluid flow path from the fluid infusion device to the user, and a sealing element coupled to the base plate and overlying at least a portion of the hollow fluid delivery needle. The sealing element includes a base section, a tip section extending from the base section, a retractable body section between the base section and the tip section, and a needle cavity formed in the retractable body section and continuing through the base section to define a needle opening in the base section. The needle cavity is sized to receive the hollow fluid delivery needle, and the needle cavity defines internal relief features of the retractable body section. The fluid infusion device also includes a removable fluid reservoir comprising a fluid delivery port to receive a tip of the hollow fluid delivery needle. The internal relief features promote deformation of the sealing element and retraction of the sealing element over the hollow fluid delivery needle when the removable fluid reservoir is engaged with the sealing element and the hollow fluid delivery needle. The internal relief features also cause the sealing element to automatically extend over the hollow fluid delivery needle, and cause the sealing element to assume a nominal state when the removable fluid reservoir is removed from the sealing element and the hollow fluid delivery needle.

Yet another embodiment of a fluid infusion device is also provided here. The fluid infusion device includes a base plate, a hollow fluid delivery needle coupled to the base plate to provide a fluid flow path for the medication fluid, and a sealing element coupled to the base plate and overlying at least a portion of the hollow fluid delivery needle. The sealing element includes a base section, a tip section extending from the base section, and a retractable body section between the base section and the tip section. The fluid infusion device also includes a fluid reservoir having a fluid chamber, a fluid delivery port coupled to the fluid chamber, and at least one vent hole formed in the fluid delivery port. The at least one vent hole provides a venting conduit from inside the fluid chamber to outside the fluid chamber. The fluid delivery port engages and cooperates with the sealing element and the hollow fluid delivery needle such that the tip section of the sealing element is urged against the fluid delivery port to seal the at least one vent hole.

An alternative embodiment of a fluid reservoir is also presented here. The fluid reservoir includes a main body section that defines a fluid chamber for the medication fluid, a fluid delivery port coupled to and extending from the main body section, the fluid delivery port having a fluid conduit and a pressure vent defined therein, and a septum located in the fluid delivery port and having a nominal non-pierced state forming a fluid seal within the fluid conduit. The pressure vent provides a venting conduit from inside the fluid chamber to outside the fluid chamber, and the pressure vent terminates at an exterior surface of the fluid delivery port. The exterior surface is contoured to mate with a resilient sealing element of the fluid infusion device to seal the pressure vent.

Also disclosed here is an embodiment of a sealing assembly for a fluid infusion device having a hollow fluid delivery needle, a retractable sealing element surrounding the hollow fluid delivery needle, and a fluid reservoir. The sealing assembly includes a fluid delivery port for the fluid reservoir, the fluid delivery port comprising a first sealing surface, a pressure vent formed in the fluid delivery port to provide a venting conduit for a fluid chamber of the fluid reservoir, the pressure vent terminating at the first sealing surface, and a tip section for the retractable sealing element. The tip section has a second sealing surface to mate with the first sealing surface, wherein the first sealing surface and the second sealing surface are urged together to form a fluid seal for the pressure vent when the fluid reservoir is engaged with the hollow fluid delivery needle and the sealing element.

Another alternative embodiment of a fluid reservoir is presented here. The fluid reservoir includes a main body section that defines a fluid chamber for the medication fluid, and a fluid delivery port coupled to and extending from the main body section. The fluid delivery port includes a fluid conduit that communicates with the fluid chamber, and the fluid delivery port terminates at a port opening. The fluid reservoir also includes a septum movably coupled to the fluid delivery port. The septum is movable between a sealed position where the septum forms a circumferential seal around the port opening, and a vented position that permits fluid to flow out of the fluid delivery port via the port opening.

Yet another alternative embodiment of a fluid reservoir is presented here. The fluid reservoir includes a main body section that defines a fluid chamber for the medication fluid, and a fluid delivery port coupled to and extending from the main body section. The fluid delivery port has a fluid conduit that communicates with the fluid chamber, and the fluid delivery port terminates at a port opening. The fluid reservoir also includes a valve sleeve movably coupled to the fluid delivery port, wherein the fluid delivery port and the valve sleeve cooperate to accommodate translational movement of the valve sleeve relative to the fluid delivery port. A septum is located within the valve sleeve and is movable in concert with the valve sleeve between a sealed position and a vented position.

Also provided here is another alternative embodiment of a fluid infusion device that delivers a medication fluid to a body. The fluid infusion device includes a base plate, a hollow fluid delivery needle coupled to the base plate to provide a fluid flow path for the medication fluid, and a fluid reservoir. The fluid reservoir includes a main body section that defines a fluid chamber for the medication fluid, a fluid delivery port coupled to and extending from the main body section, and a septum coupled to the fluid delivery port. The fluid delivery port has a fluid conduit that communicates with the fluid chamber, and the fluid delivery port terminates at a port opening. The septum translates relative to the port opening and is movable between a sealed position and a vented position. In the sealed position, the hollow fluid delivery needle engages the septum and urges the septum against the port opening to form a circumferential seal around the port opening. In the vented position, the hollow fluid delivery needle is disengaged from the septum.

Yet another embodiment of a fluid infusion device is also provided here. The fluid infusion device includes a fluid reservoir having a main body section that defines a fluid chamber for the medication fluid, and also having a fluid delivery port coupled to and extending from the main body section. The fluid delivery port has a fluid conduit that communicates with the fluid chamber, and the fluid delivery port terminates at an unsealed port opening. The fluid infusion device also includes a self-sealing reservoir port receptacle for the fluid delivery port. The port receptacle has an inlet to receive the fluid delivery port, a valve chamber in fluid communication with the inlet, a valve element located in the valve chamber, and an outlet in fluid communication with the valve chamber. The valve element is biased toward the inlet into a sealed position to form a fluid seal between the valve element and the inlet, and the outlet provides a fluid flow path for the medication fluid. Engagement of the fluid delivery port with the inlet causes an end of the fluid delivery port to move the valve element from the sealed position to an opened position to accommodate flow of the medication fluid into the valve chamber.

An alternative embodiment of a sealing assembly for a fluid infusion device is also presented here. The sealing assembly includes a reservoir port receptacle, an inlet formed in the reservoir port receptacle to receive a fluid delivery port of a fluid reservoir that contains the medication fluid, and a valve chamber formed in the reservoir port receptacle and in fluid communication with the inlet, a valve element located in the valve chamber, a resilient compression element located in the valve chamber to bias the valve element toward the inlet, and an outlet formed in the reservoir port receptacle to provide a fluid flow path for the medication fluid.

Another embodiment of a fluid infusion device is also presented here. The fluid infusion device includes a base plate, a delivery conduit coupled to the base plate, wherein the delivery conduit provides the medication fluid to the body, and a self-sealing reservoir port receptacle located on the base plate. The self-sealing reservoir port receptacle includes an inlet to receive a fluid delivery port of a fluid reservoir, a valve chamber in fluid communication with the inlet, a valve element located in the valve chamber, and an outlet between the valve chamber and the delivery conduit. When the fluid delivery port is disengaged from the self-sealing reservoir port receptacle, the valve element is biased toward the inlet into a sealed position to form a fluid seal between the valve element and the inlet. The outlet provides a fluid flow path for the medication fluid. When the fluid delivery port is engaged with the self-sealing reservoir port receptacle, an end of the fluid delivery port moves the valve element from the sealed position to an opened position to accommodate flow of the medication fluid from the fluid reservoir into the valve chamber.

Also presented here is an alternative embodiment of a fluid reservoir for a fluid infusion device that delivers a medication fluid to a body. The fluid reservoir includes a main body section that defines a fluid chamber for the medication fluid, a hollow needle extending from the main body section and defining a fluid conduit that communicates with the fluid chamber, the hollow needle terminating at a needle end, and a needle hood extending from the main body section and at least partially surrounding the hollow needle. The needle hood terminates at a lip that extends further from the main body section than the needle end.

Yet another alternative embodiment of a fluid infusion device is also provided here. The fluid infusion device includes a base plate, a delivery conduit coupled to the base plate, wherein the delivery conduit provides the medication fluid to the body, and a fluid reservoir. The fluid reservoir has a main body section that defines a fluid chamber for the medication fluid, a hollow needle extending from the main body section and in fluid communication with the fluid chamber, and a needle hood extending from the main body section and at least partially surrounding the hollow needle. The fluid infusion device also includes a reservoir port receptacle located on the base plate and comprising mating structure to engage and mate with the needle hood, a sealing element to receive the hollow needle and form a seal around an exterior surface of the hollow needle, and an outlet conduit at least partially defined by the sealing element, wherein the outlet conduit is coupled to the delivery conduit.

Also presented here is another embodiment of a fluid infusion device that delivers a medication fluid to a body. The fluid infusion device includes a fluid reservoir having a main body section that defines a fluid chamber for the medication fluid, and having a hollow needle extending from the main body section and in fluid communication with the fluid chamber. The fluid infusion device also includes a reservoir port receptacle having a sealing element, and having mating structure to engage the fluid reservoir in an aligned orientation for introducing the hollow needle into the sealing element to form a seal around an exterior surface of the hollow needle.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 21 is a longitudinal cross-sectional view of a fluid reservoir and a self-sealing reservoir port receptacle suitable for use with a fluid infusion device;

FIG. 22 is an end view of the fluid reservoir as viewed from the perspective of line 22-22 in FIG. 21;

DETAILED DESCRIPTION

Figure 1:
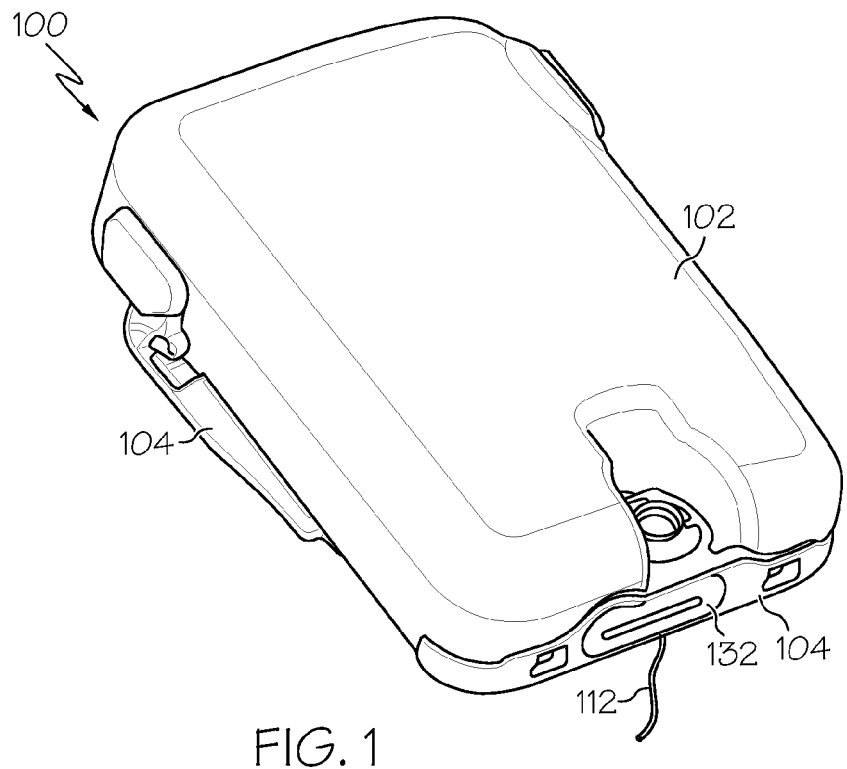
FIG. 1 is a perspective view of an embodiment of a fluid infusion device.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

Various embodiments presented here are related to a sealing element suitable for use with a fluid reservoir and a fluid delivery needle of the type found in fluid infusion systems. In certain embodiments, the sealing element includes at least one slit formed in its tip to accommodate a hollow needle. When a fluid reservoir is introduced and coupled to the needle, the port of the fluid reservoir and/or another structural feature of the reservoir urges the sealing element to retract over the needle such that the end of the needle penetrates the slit, protrudes from the tip of the sealing element, and enters the fluid reservoir. Upon fluid connection in this manner, the needle penetrates the tip of the sealing element, which in turn outwardly expands the material (e.g., silicone) of the sealing element near the tip. The reservoir port that receives the sealing element is sized and configured such that expansion of the sealing element forms a radial seal between the inner surface of the reservoir port and the sealing element. Further and complete installation of the reservoir onto the needle also creates a secondary backup face seal between the opening of the reservoir port and the sealing element.

Additional embodiments of various fluid reservoir configurations, needle sealing arrangements, and fluid interface designs are also presented here. For example, a number of vented fluid reservoir embodiments are described below, where a pressure vent is incorporated into the fluid reservoir to facilitate the equalization of pressure that may otherwise be present inside of the fluid reservoir and, therefore, to reduce the likelihood of accidental fluid delivery caused by the build-up of internal pressure.

In addition, a "needleless" embodiment is presented here. In lieu of a fluid delivery needle, a fluid reservoir is suitably configured to interact with a sealing component or feature of a base plate of the fluid infusion device. The sealing component includes a valve member (e.g., a ball valve) that opens to accommodate fluid delivery from the fluid reservoir when the reservoir is introduced to the base plate. When the reservoir is removed, the valve member automatically seals the flow path.

Various embodiments of a fluid reservoir having a "hooded" or shielded needle or needle-like structure are also provided. The reservoir needle is designed to deliver the medication fluid to a corresponding fluid receptacle of the fluid infusion device. The fluid receptacle includes a sealing element that receives the reservoir needle and creates a fluid seal with the reservoir.

The following description relates to a fluid infusion device of the type used to treat a medical condition of a patient. The infusion device is used for infusing fluid into the body of a user. The non-limiting examples described below relate to a medical device used to treat diabetes (more specifically, an insulin pump), although embodiments of the disclosed subject matter are not so limited. Accordingly, the infused medication fluid is insulin in certain embodiments. In alternative embodiments, however, many other fluids may be administered through infusion such as, but not limited to, disease treatments, drugs to treat pulmonary hypertension, iron chelation drugs, pain medications, anti-cancer treatments, medications, vitamins, hormones, or the like. For the sake of brevity, conventional features and characteristics related to infusion system operation, insulin pump and/or infusion set operation, fluid reservoirs, and fluid syringes may not be described in detail here. Examples of infusion pumps and/or related pump drive systems used to administer insulin and other medications may be of the type described in, but not limited to: United States patent application number 2009/0299290 A1; United States patent application number 2008/0269687; U.S. Pat. No. 7,828,764; and U.S. Pat. No. 7,905,868 (the entire content of these patent documents is incorporated by reference herein).

Retractable Needle Sealing Element

Figure 2:
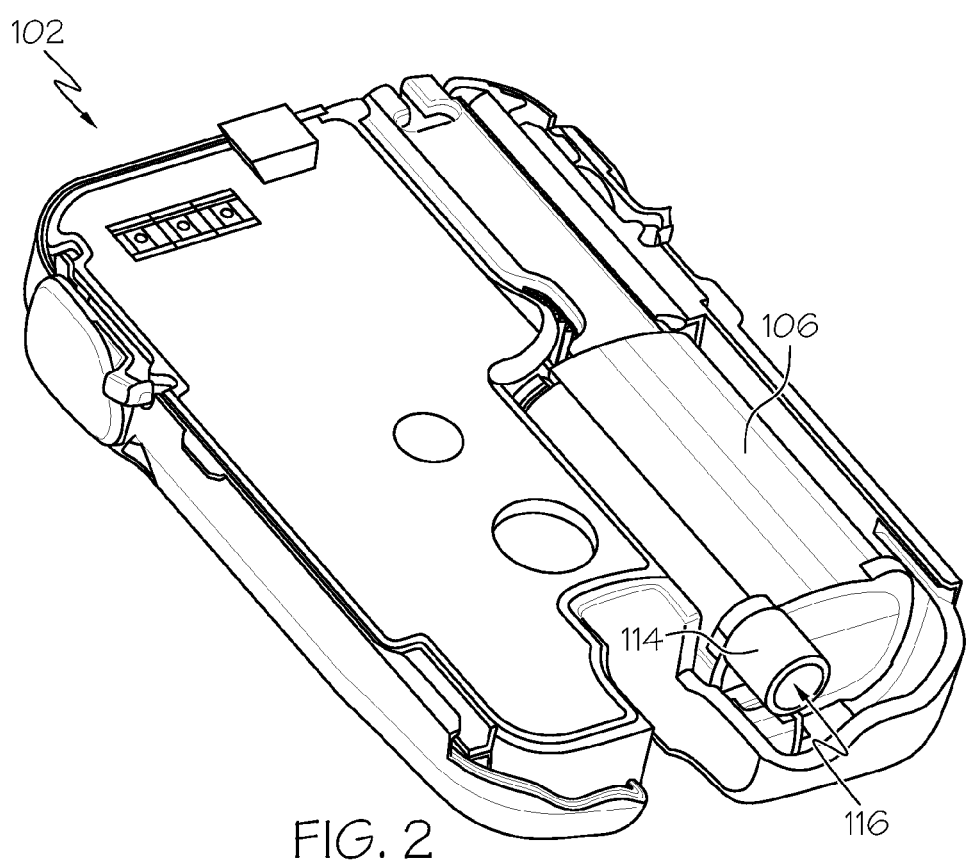
FIG. 2 is a perspective view that depicts internal structure of the durable housing of the fluid infusion device shown in FIG. 1.
Figure 3:
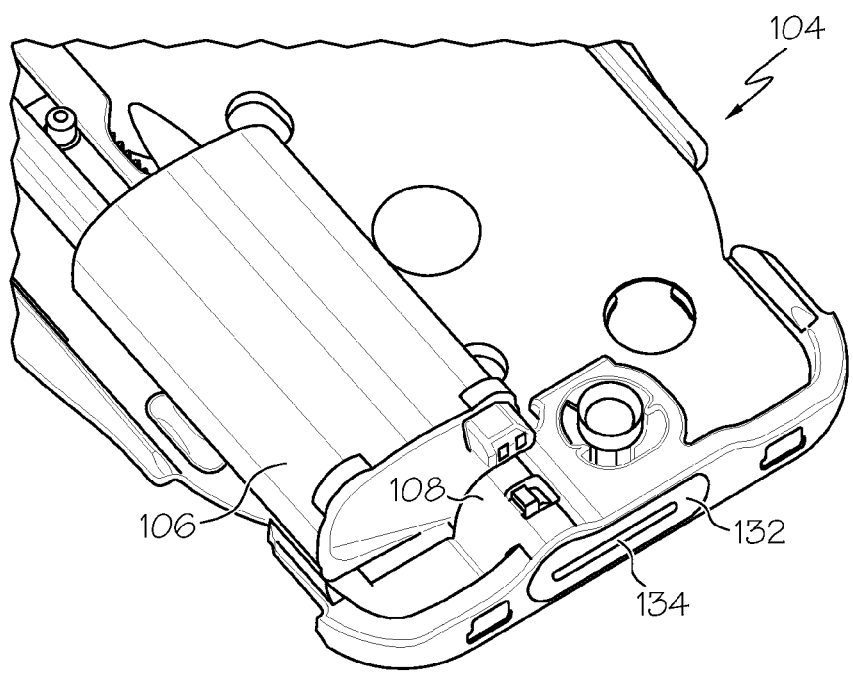
FIG. 3 is a perspective view that depicts internal structure of the base plate of the fluid infusion device shown in FIG. 1.
Figure 4:
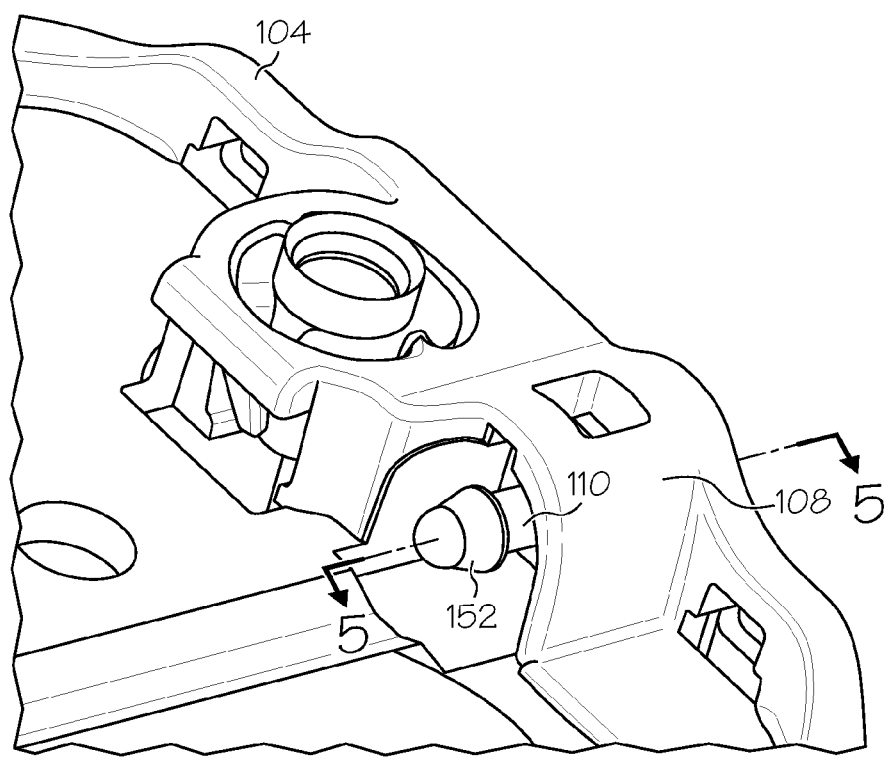
FIG. 4 is a perspective view that depicts the reservoir port receptacle and a sealing element of the fluid infusion device shown in FIG. 1.

FIG. 1 is a perspective view of an exemplary embodiment of a fluid infusion device 100. The fluid infusion device 100 includes two primary components that are removably coupled to each other: a durable housing 102; and a base plate 104. The fluid infusion device 100 also includes or cooperates with a removable/replaceable fluid reservoir 106. For the illustrated embodiment, the fluid reservoir 106 mates with, and is received by, the durable housing 102. In alternate embodiments, the fluid reservoir 106 mates with, and is received by, the base plate 104. FIG. 2 is a perspective view that depicts internal structure of the durable housing 102, FIG. 3 is a perspective view that depicts internal structure of the base plate 104, and FIG. 4 is a perspective view that depicts a reservoir port receptacle 108 and a sealing element 110 of the fluid infusion device 100.

The base plate 104 is designed to be temporarily adhered to the skin of the patient using, for example, an adhesive layer of material. After the base plate is affixed to the skin of the patient, a suitably configured insertion device or apparatus may be used to insert a fluid delivery needle or cannula 112 (see FIG. 1) into the body of the patient. The cannula 112 functions as one part of the fluid delivery path associated with the fluid infusion device 100, as is well understood.

FIG. 1 depicts the durable housing 102 and the base plate 104 coupled together. In practice, the durable housing 102 and/or the base plate 104 may include features, structures, or elements to facilitate removable coupling (e.g., pawls, latches, rails, slots, keyways, buttons, or the like). As shown in FIG. 2, the durable housing 102 is designed to receive the removable fluid reservoir 106 and to retain the fluid reservoir 106 in a particular position and orientation. Moreover, the durable housing 102 is configured to secure to the base plate 104 in a specified orientation to engage the fluid reservoir 106 with the reservoir port receptacle 108 (see FIG. 3). For this particular embodiment, the durable housing 102 contains, among other components, a drive motor, a battery, a threaded drive shaft for the fluid reservoir, one or more integrated circuit chips and/or other electronic devices (not shown). In particular embodiments, the fluid infusion device 100 includes certain features to orient, align, and position the durable housing 102 relative to the base plate 104 such that when the two components are coupled together the fluid reservoir 106 is urged into the reservoir port receptacle 108 to engage the sealing assembly and establish a fluid seal, as described in more detail below.

The durable housing 102 and the base plate 104 are cooperatively configured to accommodate removable coupling of the durable housing 102 to the base plate 104. The removable nature of the durable housing 102 enables the patient to replace the fluid reservoir 106 as needed. Moreover, the durable housing 102 can be removed (while leaving the base plate 104 adhered to the patient) to allow the patient to swim, shower, bathe, and participate in other activities that might otherwise damage or contaminate the durable housing 102. When the durable housing 102 is removed from the base plate 104, the fluid reservoir 106 is disengaged from the reservoir port receptacle 108, the fluid flow path is broken, and the base plate 104 will appear as shown in FIG. 4.

Figure 5:
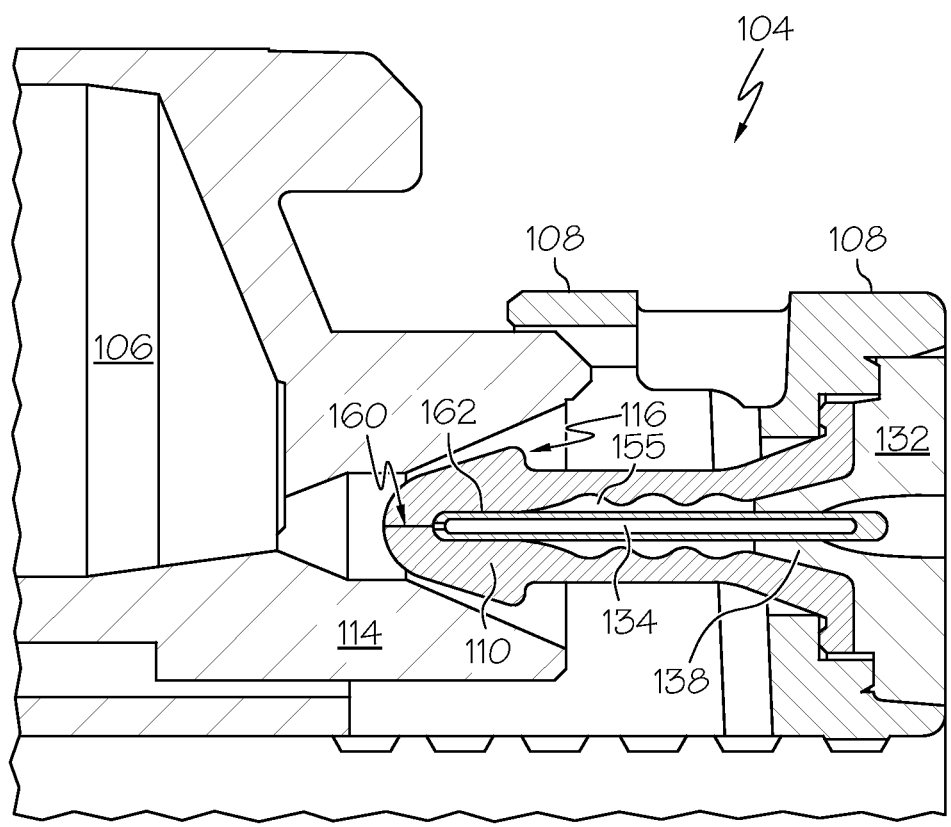
FIG. 5 is a cross-sectional and partially phantom view of a portion of the fluid infusion device, corresponding to a view along line 5-5 in FIG. 4.

The fluid reservoir 106 includes a fluid delivery port 114 that cooperates with the reservoir port receptacle 108. FIG. 3 depicts the fully installed position of the fluid reservoir 106 relative to the base plate 104 and the reservoir port receptacle 108 (for ease of illustration, the durable housing 102 is not shown in FIG. 3). The fluid delivery port 114 may include a pierceable septum if the fluid reservoir 106 is a prefilled unit. Alternatively, the fluid delivery port 114 may include a vented opening to accommodate filling of the fluid reservoir 106 by the patient, a doctor, a caregiver, or the like. The fluid delivery port 114 has an interior 116 defined therein. As shown in FIG. 5, the interior 116 is shaped, sized, and otherwise configured to receive the sealing element 110 when the fluid reservoir 106 is engaged with the reservoir port receptacle 108. In certain embodiments, the interior 116 is conical, tapered, and/or funnel-shaped, as best shown in FIG. 5. This preferred shape of the interior 116 makes it easy for the sealing element 110 to mate with the fluid delivery port 114 when the durable housing 102 is coupled to the base plate 104.

The sealing element 110 forms part of a sealing assembly 130 for the fluid infusion device 100. The sealing assembly 130 as referred to here may also include the base plate 104 (or a portion thereof) and/or other structure or elements that cooperate with the sealing element 110. These additional components will be described with reference to FIG. 5, which is a cross-sectional and partially phantom view of a portion of the fluid infusion device 100 (corresponding to the view taken from line 5-5 in FIG. 4) and with reference to FIG. 6, which is an exploded perspective view of the sealing assembly 130. The illustrated embodiment of the sealing assembly 130 generally includes, without limitation: the sealing element 110; a mounting cap 132; and a hollow fluid delivery needle 134. It should be appreciated that a portion of the base plate 104 (e.g., the reservoir port receptacle 108 and/or the end portion of the base plate 104 that receives the sealing element 110 and the mounting cap 132) may be considered to be part of the sealing assembly 130.

Figure 6:
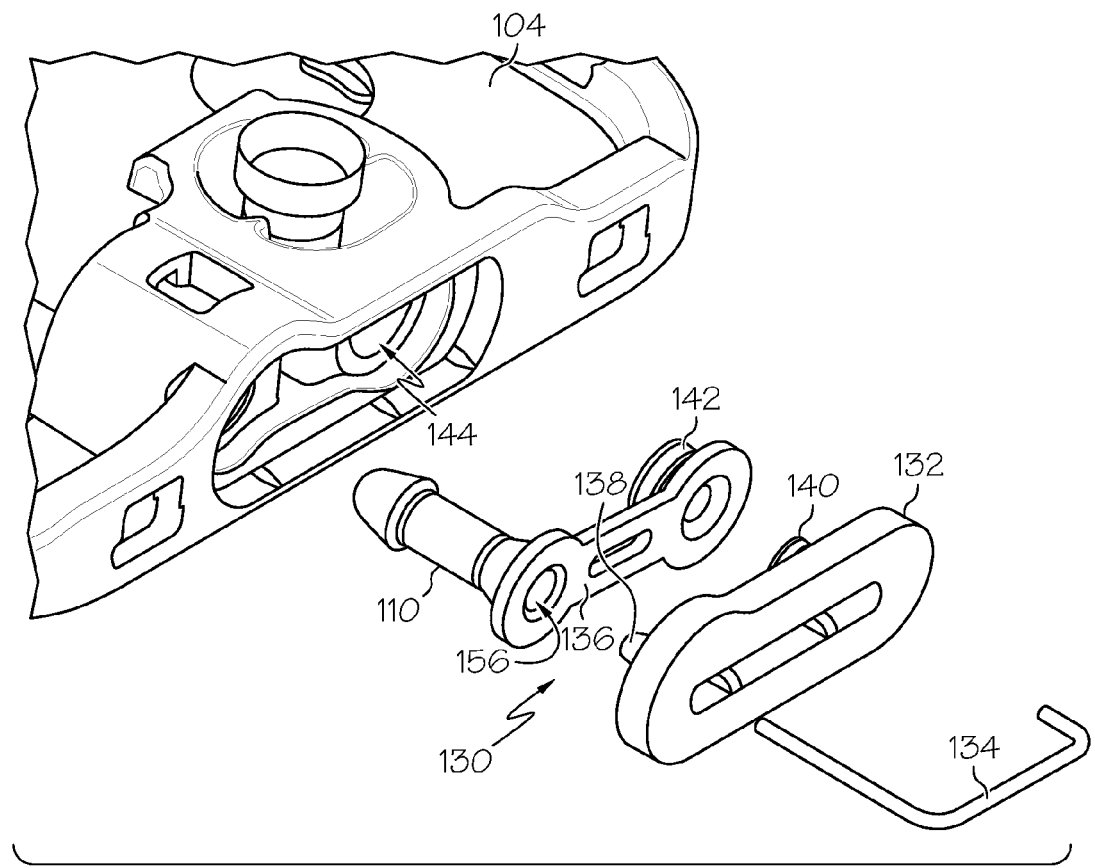
FIG. 6 is an exploded perspective view of a sealing assembly suitable for use with the fluid infusion device shown in FIG. 1.
Figure 7:
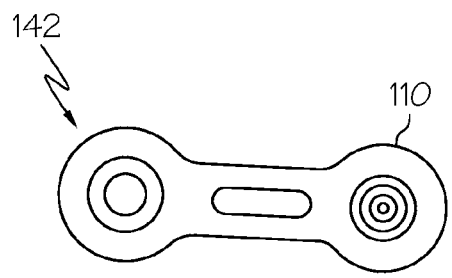
FIG. 7 is a plan view of the sealing element shown in FIG. 6, as viewed from its base end.
Figure 8:
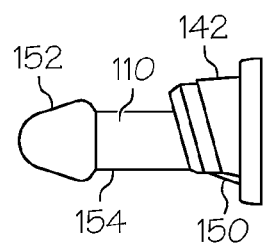
FIG. 8 is a side elevation view of the sealing element shown in FIG. 6.
Figure 9:
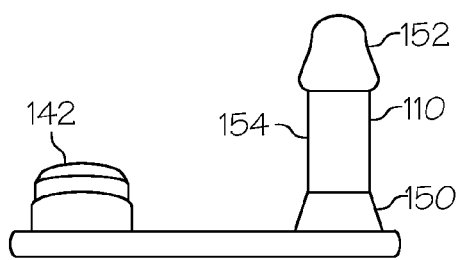
FIG. 9 is a front elevation view of the sealing element shown in FIG. 6.
Figure 10:
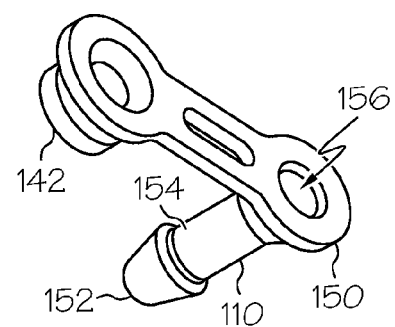
FIG. 10 is a perspective view of the sealing element shown in FIG. 6.

The sealing assembly 130 may be formed by coupling the sealing element 110 and the hollow fluid delivery needle 134 to the mounting cap 132. In turn, the mounting cap 132 may be secured to the base plate 104 (see FIG. 1 and FIG. 3). The sealing element 110 and the hollow fluid delivery needle 134 may be secured to the mounting cap 132 using an adhesive, a bonding or welding agent, by a compression or snap fitting arrangement, or the like. The bottom surface 136 of the sealing element 110 (see FIG. 6) forms a fluid seal with a mating surface of the mounting cap 132. In certain embodiments, the mounting cap 132 includes a hollow protrusion 138 (which may be conical in shape) that extends into, and forms a fluid seal with, the base section of the sealing element 110, as shown in FIG. 5. A portion of the hollow fluid delivery needle 134 extends through the hollow protrusion 138 and into the sealing element 110. As shown in FIG. 6, the hollow fluid delivery needle 134 for this particular embodiment is "J" shaped to provide a fluid flow path from the sealing element 110, across the length of the mounting cap 132, and into an outlet port 140 of the mounting cap 132. The outlet port 140 leads to a second sealing element 142 (which may be integrally formed with the sealing element 110, as shown), which in turn leads into a fluid chamber 144 defined in the base plate 104. The fluid chamber 144 is fluidly coupled to the cannula 112 (FIG. 1) such that when a plunger of the fluid reservoir 106 is actuated, the fluid is expelled from the fluid reservoir 106, through the hollow fluid delivery needle 134, into the fluid chamber 144, and into the body of the patient via the cannula 112.

Figure 11:
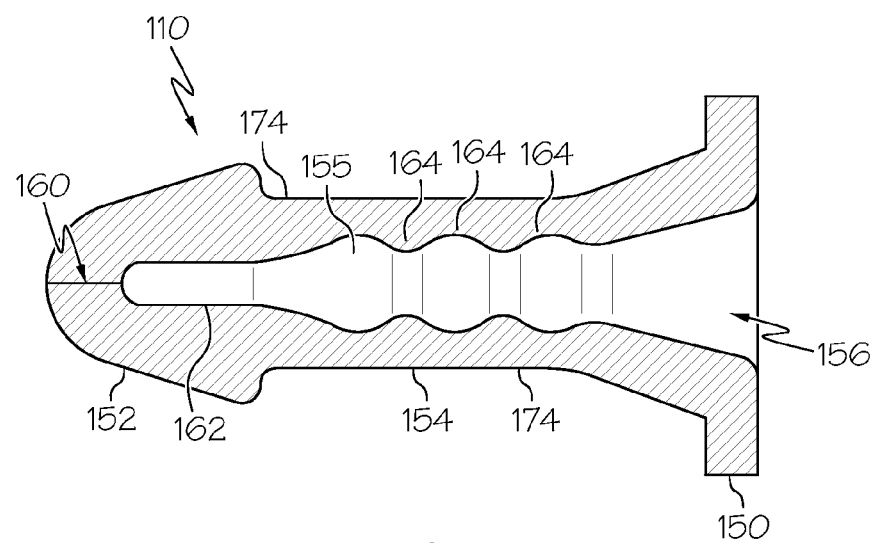
FIG. 11 is a longitudinal cross-sectional view of the sealing element shown in FIG. 6.

FIGS. 7-10 show the sealing element 110 and the second sealing element 142 in more detail, and FIG. 11 shows the sealing element 110 by itself in cross-section. The sealing element 110 and the second sealing element 142 may be integrally formed as a one-piece component from a resilient and deformable material, such as rubber, urethane, or the like. In certain embodiments, the sealing element 110 and the second sealing element 142 are formed from a pliable silicone material. The material used for the sealing element and the second sealing element 142 is selected to be resistant to the fluid being delivered, biocompatible, and capable of being sterilized after manufacturing. The following description focuses on the configuration, characteristics, and functionality of the sealing element 110 (the figures include the second sealing element 142 for the sake of completeness and for consistency with the exemplary embodiment).

The sealing element 110 includes a base section 150, a tip section 152 extending from the base section 150, and a retractable body section 154 between the base section 150 and the tip section 152. In practice, the sealing element 110 is a one-piece component and, accordingly, the base section 150, the tip section 152, and the retractable body section 154 are integrally formed and continuous with one another. Referring to FIG. 11, the sealing element 110 includes a needle cavity 155 formed therein. More specifically, the needle cavity 155 is formed within the retractable body section 154, and it continues through the base section 150 to define a needle opening 156 in the base section 150. The exemplary embodiment depicted in the figures includes a tapered or conical shaped needle opening 156 that mates with the outer contour of the hollow protrusion 138 (see FIG. 5), which in turn accommodates the hollow fluid delivery needle 134. As shown in FIG. 5, the needle cavity 155 is shaped, sized, and configured to receive the hollow fluid delivery needle 134.

The base section 150 generally corresponds to the portion of the sealing element 110 that is coupled to the base plate 104 (by way of the mounting cap 132). Notably, the mounting cap 132 and the hollow fluid delivery needle 134 are coupled to the base plate 104 in a substantially fixed and rigid manner such that the hollow fluid delivery needle 134 protrudes from the mounting cap 132 and extends within the reservoir port receptacle 108 (see FIG. 4). The sealing element 110, however, is a pliable and deformable feature. FIG. 4 depicts the sealing element 110 in its natural nominal state without the fluid reservoir 106 in place. In this nominal state, the tip section 152 of the sealing element 110 extends slightly beyond the lip of the reservoir port receptacle 108. The sealing element 110 is configured to retract over the hollow fluid delivery needle 134 when the fluid reservoir 106 engages the base plate 104 (in FIG. 3 the fluid reservoir 106 is fully engaged with the reservoir port receptacle 108).

The tip section 152 may be mushroom or barb shaped in various embodiments, as shown in FIGS. 8-11. The barbed shape of the tip section 152 promotes entry and seating of the sealing element 110 into the fluid delivery port 114 of the fluid reservoir 106. Moreover, the barbed shape configuration helps to establish a good radial seal between the sealing element 110 and the interior 116 of the fluid delivery port 114 (described in more detail below).

Referring to FIG. 5 and FIG. 11, the sealing element 110 may also include at least one self-sealing slit 160, slot, opening, or hole formed in the tip section 152 to accommodate the hollow fluid delivery needle 134 when the sealing element is in a retracted position. The self-sealing slit 160 may be realized as a very fine slice or puncture formed in the tip section 152 for purposes of guiding the end of the hollow fluid delivery needle 134 through the material of the sealing element 110 as needed. The self-sealing slit 160 is preferred over an embodiment that relies on repeated punctures of the tip section 152 with a sharp or pointed needle. For this particular embodiment, a flat or blunt ended hollow fluid delivery needle 134 can be utilized because the self-sealing slit 160 provides a pre-existing pathway through the tip section 152.

The self-sealing slit 160 expands to accommodate passage of the hollow fluid delivery needle 134, and it automatically returns to a "closed" and sealed state when the fluid reservoir 106 is removed from the base plate 104. The sealed state is depicted in FIG. 5—the hollow fluid delivery needle 134 is fully enclosed within the sealing element 110 and the end of the hollow fluid delivery needle 134 is positioned behind the self-sealing slit 160. More specifically, the sealing element 110 is overlying the protruding portion of the hollow fluid delivery needle 134, which is located within the retractable body section 154. In this state, the self-sealing slit 160 closes to inhibit fluid ingress into the needle cavity 155 and to protect the hollow fluid delivery needle 134 from contamination.

The illustrated embodiment of the sealing element 110 also includes an integral guide channel 162 formed in the tip section 152. The guide channel 162 is in communication with the needle cavity 155 and the self-sealing slit 160, as best shown in FIG. 11. The guide channel 162 may be realized as an opening or neck region having a smaller dimension (e.g., diameter) than the end of the needle cavity 155, but a larger dimension than the self-sealing slit 160. This arrangement and configuration enables the guide channel 162 to guide/lead the tip of the hollow fluid delivery needle 134 into the self-sealing slit 160 during retraction of the sealing element 110 over the hollow fluid delivery needle 134. In practice, the guide channel 162 increases the likelihood of the hollow fluid delivery needle 134 entering the self-sealing slit 160 rather than "catching" and puncturing the material forming the tip section 152.

Referring to FIG. 11, the needle cavity 155 is suitably configured such that it defines internal relief features 164 and/or an internal relief structure of the retractable body section 154. In operation, the internal relief features 164 facilitate retraction of the sealing element 110 over the hollow fluid delivery needle 134 in response to a longitudinal force applied to the tip section 152. Longitudinal force of this type may be imparted to the tip section 152 when the durable housing 102 is coupled to the base plate 104 and, consequently, when the fluid delivery port 114 of the fluid reservoir 106 engages the reservoir port receptacle 108 of the base plate 104 (see FIG. 3). The internal relief features 164 also cause the sealing element 110 to be self-biasing or spring-like such that the sealing element 110 extends over and covers the hollow fluid delivery needle 134 in response to the removal of the longitudinal force. This extended position is depicted in FIGS. 5-11.

The internal relief features 164 allow the sealing element 110 to compress and deform easily when the fluid reservoir 106 is introduced. Moreover, the internal relief features 164 function as a spring when under compression. In this regard, the internal relief features 164 urge the tip section 152 outward and beyond the end of the hollow fluid delivery needle 134 when the fluid reservoir 106 is withdrawn. The specific configuration of the internal relief features 164 may vary from one embodiment to another, and the exemplary arrangement depicted in FIG. 11 is not intended to be exhaustive or otherwise limiting. As shown in FIG. 11, the internal relief features 164 may include or be arranged as an accordion structure within the needle cavity 155. Alternatively (or additionally), the internal relief features 164 may include one or a plurality of internal annular channels formed within the needle cavity 155. Alternatively (or additionally), the internal relief features 164 may include one or a plurality of internal annular ridges or ribs within the needle cavity 155. Alternatively (or additionally), the internal relief features 164 may include one or a plurality of bottleneck structures resident within the needle cavity 155. The embodiment shown in FIG. 11 includes a number of annular channels alternating with a plurality of annular ridges. This arrangement of channels and ridges results in a plurality of bottleneck regions, which in turn form the spring-like accordion structure.

Figure 12:
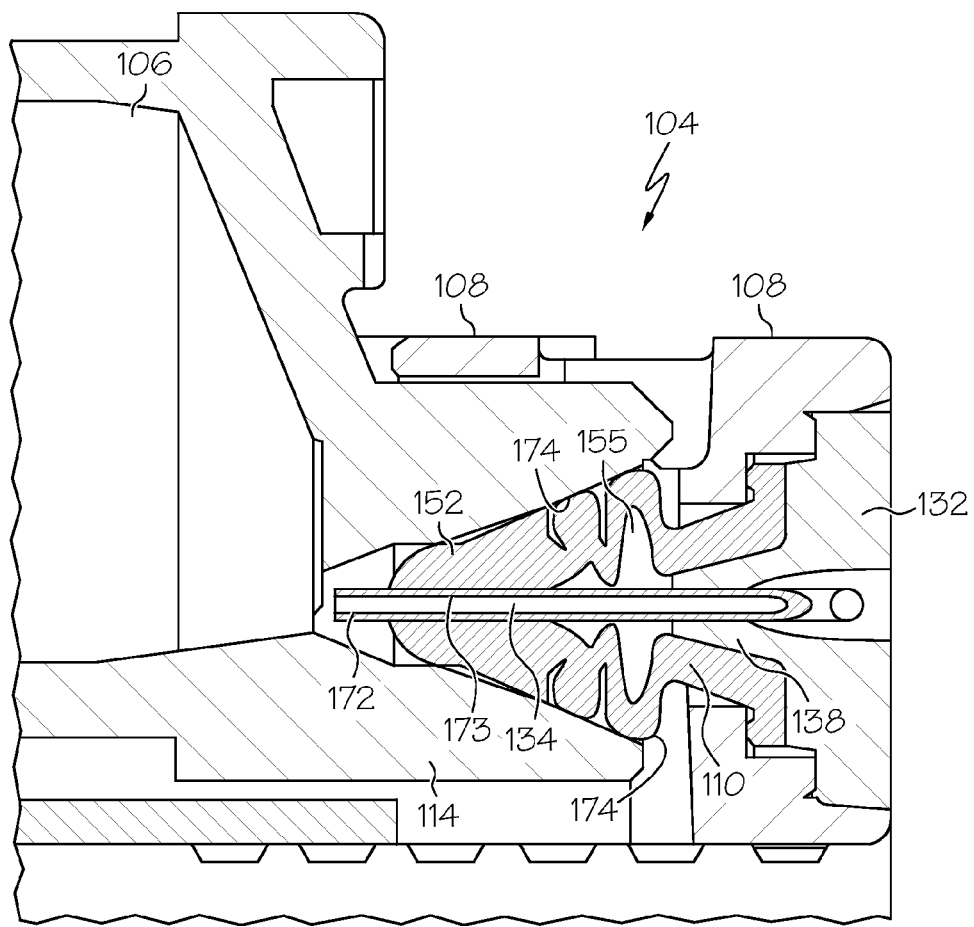
FIG. 12 is a cross-sectional and partially phantom view of a portion of the fluid infusion device, in a state where the fluid reservoir is fully engaged with the sealing element.

The mechanical characteristics, sealing characteristics, and functional aspects of the sealing element 110 will now be described with primary reference to FIGS. 4, 5, 11, and 12. The fluid infusion device 100 and, more specifically, the sealing element 110 may be manipulated into various states associated with the coupling status of the fluid reservoir 106 relative to the sealing assembly 130 (FIG. 6), the sealing element 110, the reservoir port receptacle 108, etc. The different states may also be specified with respect to the coupling status of the durable housing 102 relative to the base plate 104. In this regard, one state may be defined as the "separated" or "disconnected" or "disengaged" state where the durable housing 102 and the base plate 104 are separated from each other (or are otherwise decoupled) such that the fluid delivery port 114 is fully disengaged from the sealing element 110. FIG. 4 depicts the base plate 104 in its disconnected state. Another state may be defined as the "connected" or "engaged" state where the durable housing 102 and the base plate 104 are fully coupled together, as depicted in FIG. 1. This description assumes that the fluid reservoir 106 is properly located and installed within the durable housing 102 (see FIG. 2). Consequently, when the fluid infusion device 100 is in the connected state, the fluid delivery port 114 is received within the reservoir port receptacle 108, and the interior 116 of the fluid delivery port 114 engages the sealing element 110. FIG. 12 is a longitudinal cross-sectional view that schematically depicts the connected state of the fluid infusion device 100. In contrast, FIG. 5 shows the fluid infusion device 100 in an intermediate state where the durable housing 102 and the base plate 104 have been introduced to one another and oriented for coupling together. In this intermediate state, the fluid delivery port 114 has partially engaged the reservoir port receptacle 108, but the sealing element 110 has not yet been retracted over the hollow fluid delivery needle 134.

The sealing element 110 has a nominal state, which is depicted in FIGS. 4-11, and a retracted state, which is depicted in FIG. 12. The sealing element 110 naturally assumes its nominal state when the fluid infusion device 100 is in the disconnected state, and when the fluid infusion device 100 is in the intermediate state described above. When in the nominal state, the tip of the hollow fluid delivery needle 134 resides within the needle cavity 155 (see FIG. 5). In other words, the sealing element 110 encloses the hollow fluid delivery needle 134 when the sealing element 110 is in the nominal state. Consequently, the self-sealing slit 160 is free to return to its natural position to form a fluid seal for the needle cavity 155. Thus, when the sealing element 110 is in the nominal state, the self-sealing slit 160 inhibits fluid ingress into the needle cavity, which is desirable to prevent or minimize contamination of the hollow fluid delivery needle 134.

In contrast, the sealing element 110 is urged into its refracted state when the fluid infusion device 100 is in the connected state. The transition from the intermediate state to the connected state is associated with the application of longitudinal force (imparted by the fluid delivery port 114) to the tip section 152 of the sealing element 110. The longitudinal force is imparted to the tip section 152 when the durable housing 102 is coupled to the base plate 104—the action of coupling the durable housing 102 to the base plate 104 causes the fluid delivery port 114 to move toward the mounting cap 132, which in turn reduces the distance between the interior 116 of the fluid delivery port 114 and the mounting cap 132. In response to this reduction in distance, the sealing element 110 is deformed and crushed such that it retracts over the hollow fluid delivery needle 134. Notably, the internal relief features 164 promote the deformation and retraction of the sealing element 110 over the hollow fluid delivery needle 134 in response to force applied to the tip section 152, which is caused by forward movement of the fluid reservoir 106. Refraction of the sealing element 110 causes the tip 172 of the hollow fluid delivery needle 134 to be led through the guide channel 162 and into the self-sealing slit 160, such that the tip 172 protrudes from the tip section 152 (see FIG. 12) and such that an end section 173 of the hollow fluid delivery needle 134 resides in the self-sealing slit 160. Thus, when the removable fluid reservoir 106 is installed on the hollow fluid delivery needle 134, the tip 172 extends from the tip section 152 of the sealing element 110 and into the fluid reservoir 106.

The sealing element 110 interacts with the fluid delivery port 114 to establish a fluid seal. Referring to FIG. 11 and FIG. 12, the retractable body section 154 of the sealing element 110 has an exterior surface 174. When the sealing element 110 is in its nominal state (FIGS. 4-11), the exterior surface 174 is "relaxed" and it resembles a smooth cylindrical surface. Due to the deformable characteristics of the sealing element 110, however, the exterior surface 174 moves outward when the sealing element 110 is retracting over the hollow fluid delivery needle 134, especially when the hollow fluid delivery needle 134 protrudes from the tip section 152 and displaces the seal material. This outward movement of the exterior surface 174 corresponds to an outward expansion of the retractable body section 154. The retractable body section 154 continues to expand in this manner until it abuts the interior 116 of the fluid delivery port 114, as depicted in FIG. 12. Thus, as the tip section 152 engages the fluid delivery port 114, the sealing element 110 creates an initial seal with the fluid delivery port 114. In addition, the retractable body section 154 expands to form a radial seal with the interior 116 when the fluid reservoir 106 engages the sealing element 110 and the hollow fluid delivery needle 134. The tip section 152 of the sealing element 110 also abuts the interior 116 of the fluid delivery port 114, which enhances the fluid seal.

The internal relief features 164 facilitate compression of the sealing element 110 into the retracted state shown in FIG. 12. The internal relief features 164 also provide resiliency to enable the sealing element 110 to regain its nominal shape when the durable housing 102 is removed and, consequently, the fluid delivery port 114 is disengaged from the sealing element 110 and the hollow fluid delivery needle 134. In other words, the sealing element 110 automatically and naturally springs back into its nominal position, and extends over and covers the hollow fluid delivery needle 134, when the fluid infusion device 100 transitions from the connected state to the disconnected state. For this reason, the internal relief features 164 are preferably designed, arranged, and configured to provide spring-like characteristics to the sealing element 110.

FIGS. 13-16 depict sealing elements configured in accordance with three alternate embodiments. Any of these alternative embodiments could be utilized in lieu of the sealing element 110 described above. These alternate embodiments share many features, characteristics, and functions with the sealing element 110. For the sake of brevity, common aspects of these sealing elements will not be described in detail here.

Figure 13:
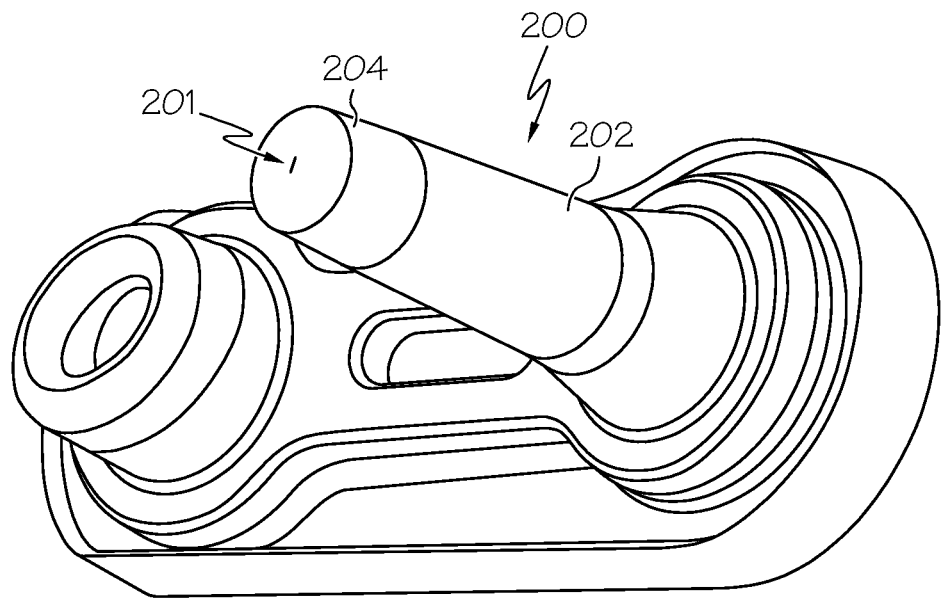
FIG. 13 is a perspective view of an alternate embodiment of a sealing element.

FIG. 13 is a perspective view of an alternate embodiment of a sealing element 200, which may be suitable for use in lieu of the sealing element 110. The sealing element 200 shares many features and characteristics with the sealing element 110 and, indeed, the internal structures of the sealing elements 110, 200 may be similar or identical. For example, the sealing element 200 also includes a self-sealing slit 201 to accommodate a needle. The sealing element 200 employs a gradually tapered retractable body section 202 that transitions smoothly and continuously with a tip section 204. In contrast, the sealing element 110 employs a barbed tip section 152.

Figure 14:
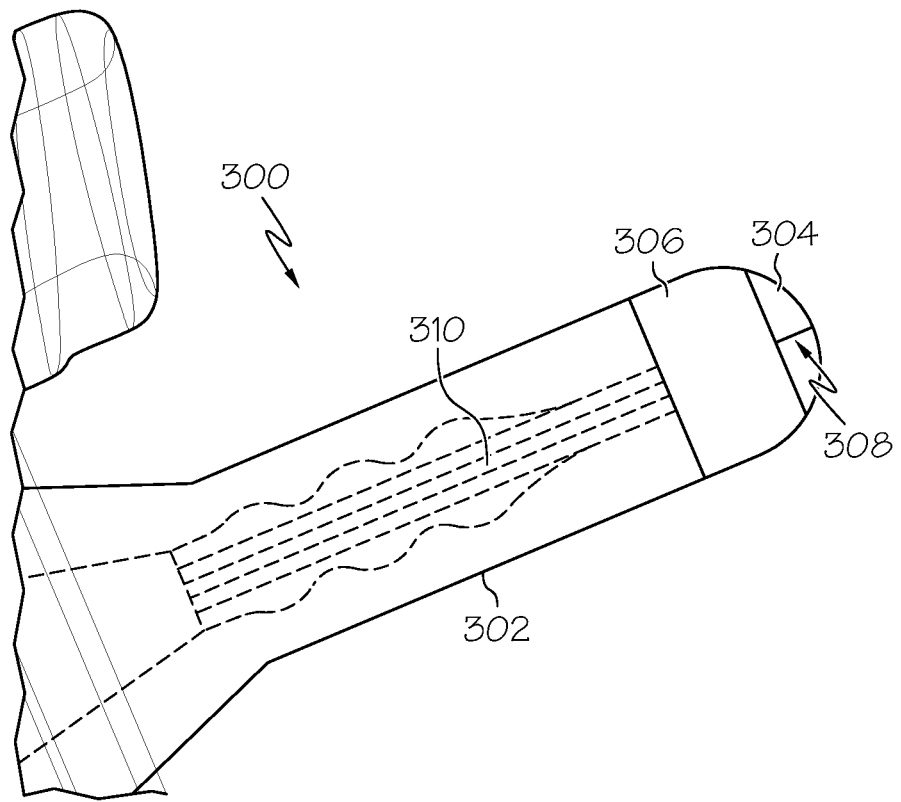
FIG. 14 is a phantom side view that depicts a portion of an alternative embodiment of a sealing element.

FIG. 14 is a phantom side view that depicts a portion of an alternate embodiment of a sealing element 300. The sealing element 300 includes a relatively straight and smooth cylindrical retractable body section 302 that transitions to a tip section 304. In contrast to the embodiments described previously, the sealing element 300 also includes a circumferential compression element 306 coupled around the tip section 304. The circumferential compression element 306 is suitably designed, shaped, and sized to impart an inward biasing force to a self-sealing slit 308 formed in the tip section 304. Consequently, when the sealing element 300 is in its natural and nominal state (as depicted in FIG. 14), the circumferential compression element 306 urges the self-sealing slit 308 closed to enhance the seal for the needle cavity 310.

In certain embodiments, the circumferential compression element 306 is realized as a physically distinct and separate component that is attached to the material that forms the bulk of the sealing element 300. For example, the circumferential compression element 306 could be affixed to the tip section 304 using an adhesive, a bonding agent, or the like. Alternatively, the circumferential compression element 306 could be coupled to the tip section 304 by way of a compression fit and/or by way of structural features that secure the circumferential compression element 306 to the tip section 304 (e.g., keyway features, tabs, ridges, or the like). In accordance with one exemplary embodiment, the circumferential compression element 306 is realized as a resilient band that resists deformation more than the material that forms the tip section 304.

Figure 15:
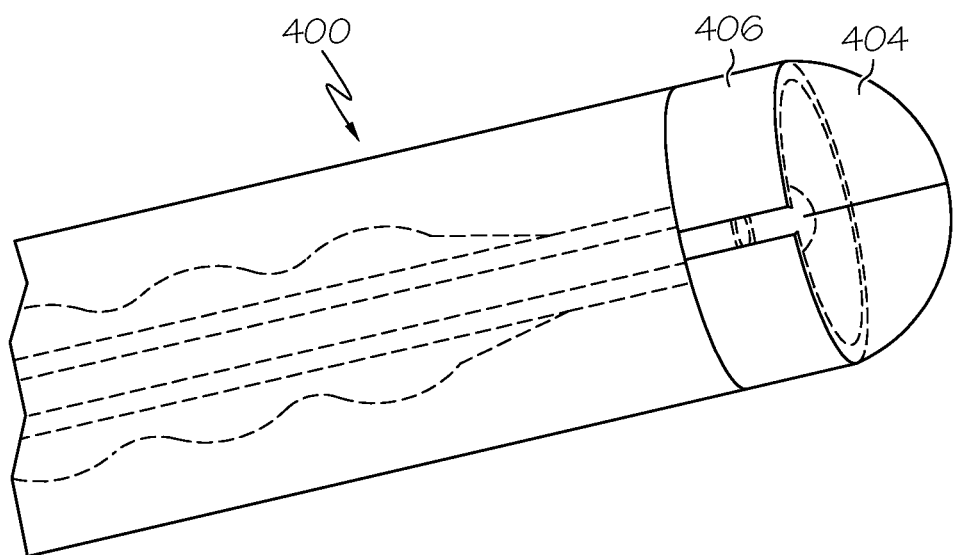
FIG. 15 is a phantom perspective view that depicts a portion of an alternative embodiment of a sealing element.

FIG. 15 is a phantom perspective view that depicts a portion of another alternate embodiment of a sealing element 400. The sealing element 400 is similar to the sealing element 300 in that it also includes a circumferential compression element 406. For this embodiment, however, the circumferential compression element 406 is realized as a rigid ring that encircles most if not all of the tip section 404. In accordance with one exemplary embodiment, the circumferential compression element 406 is realized as a metal compression ring that can be installed over the tip section 404 by bending or deforming it to achieve the desired amount of compression.

Figure 16:
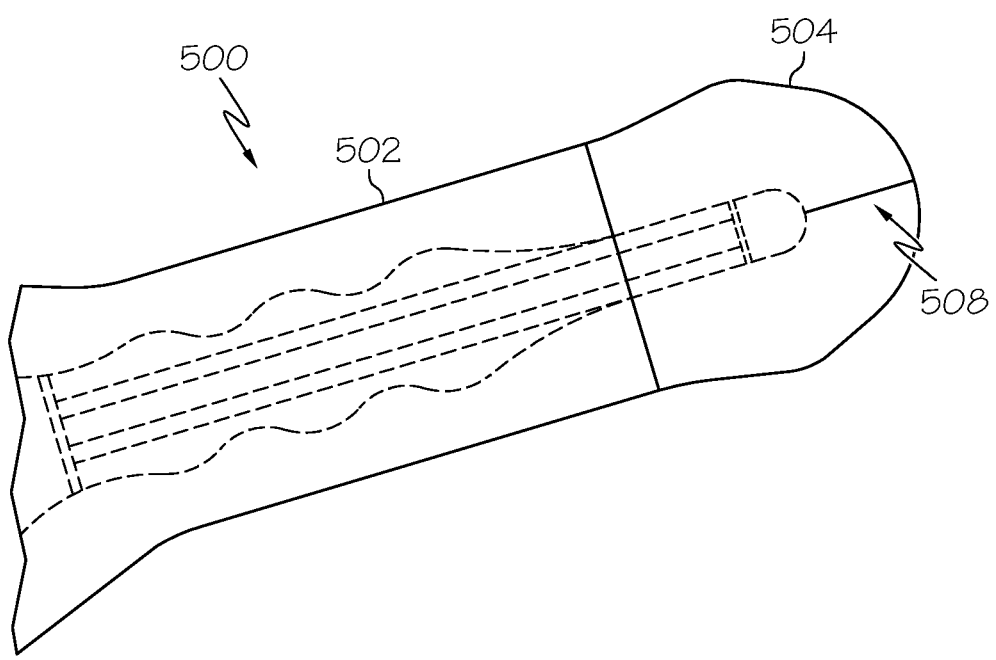
FIG. 16 is a phantom side view that depicts a portion of an alternative embodiment of a sealing element.

FIG. 16 is a phantom side view that depicts a portion of yet another alternate embodiment of a sealing element 500. The sealing element 500 includes a tip section 504 having a different shape and profile (relative to the embodiments described previously). The shape of the tip section 504 is similar to the shape of the tip section 152 in that it is wider than the retractable body section 502. This wide tip section 504 is desirable to establish a good fluid seal with the fluid reservoir. Moreover, the additional material that is used to form the wide tip section 504 serves to enhance the integrity of the self-sealing slit 508.

It should be appreciated that the specific features and characteristics shown and described above for the various exemplary embodiments are neither exclusive nor required for any given embodiment. For example, any of the exemplary sealing elements described above could be provided with or without a circumferential compression element for the tip section. As another example, the specific shape and configuration of the tip section may vary from one embodiment to another. Thus, the individual features and elements shown and described may be implemented and deployed in an embodiment of a fluid infusion device as desired to suit the needs of the particular application.

Vented Fluid Reservoirs

An open or vented fluid reservoir may be utilized to reduce or eliminate excess pressure that might otherwise be introduced into the fluid chamber of the reservoir during a filling operation. In this regard, a vented fluid reservoir allows the pressure to equalize before the reservoir is coupled to the fluid infusion device and, therefore, reduces or eliminates the likelihood of unintended fluid delivery. To this end, one embodiment described here includes a vented port or funnel to relieve the pressure in the reservoir. Another embodiment described below employs a movable septum that functions as a pressure relief valve for the fluid reservoir.

Figure 17:
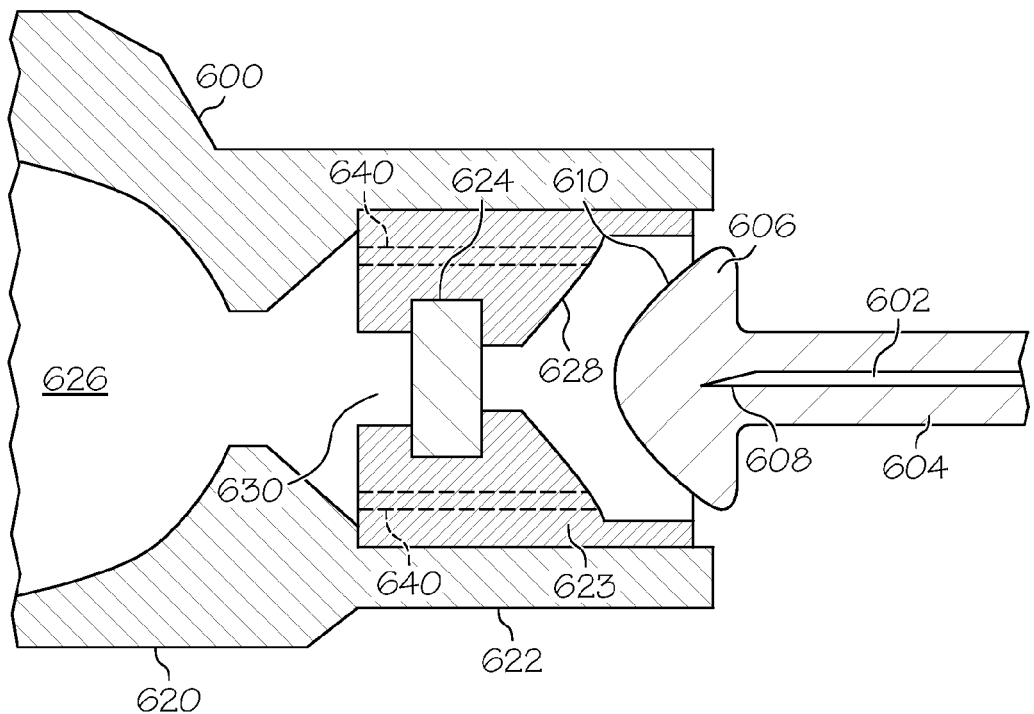
FIG. 17 is a schematic side view of an embodiment of a vented fluid reservoir.
Figure 18:
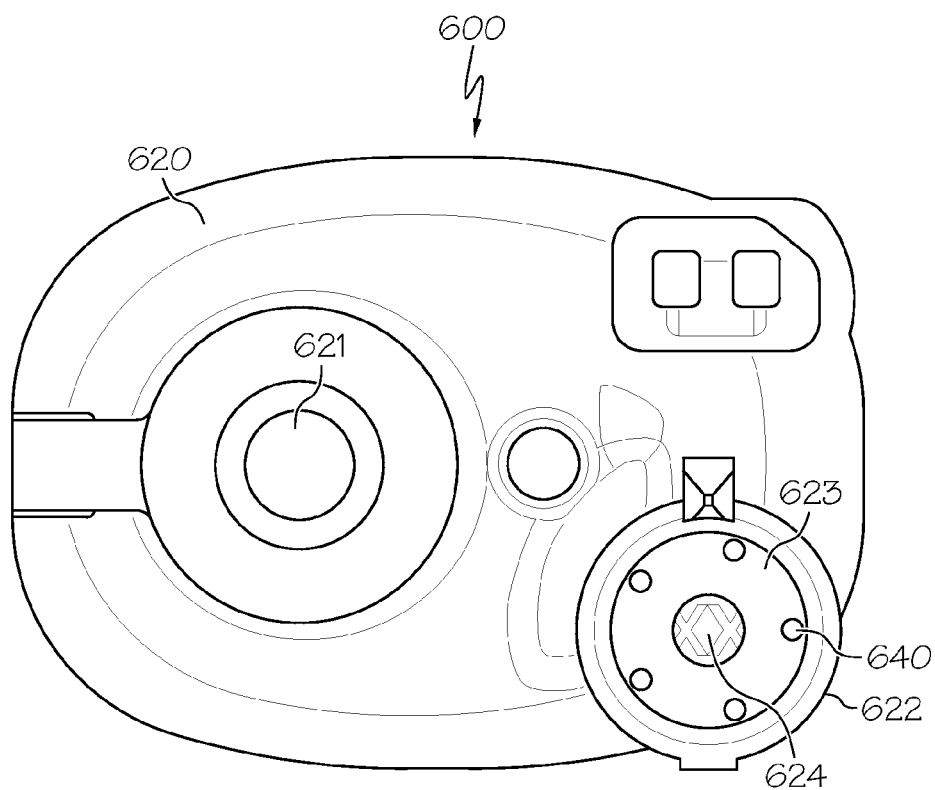
FIG. 18 is a top view of an embodiment of a vented fluid reservoir.

FIG. 17 depicts a schematic side view representation of a vented fluid reservoir 600, and FIG. 18 is a top view of an exemplary embodiment of the vented fluid reservoir 600. For ease of understanding and illustration, FIG. 17 depicts some structure in cross section and some structure in phantom. The fluid reservoir 600 may be utilized with the fluid infusion device 100 (or a slightly modified version thereof) described above with reference to FIGS. 1-6. Accordingly, common features, structures, elements, and functionality will not be redundantly described here in the context of the fluid reservoir 600.

Referring to FIG. 17, the fluid reservoir 600 may cooperate with a fluid infusion device (not shown) having a hollow fluid delivery needle 602 and a sealing element 604 overlying at least a portion of the hollow fluid delivery needle 602. The sealing element 604 may exhibit any of the features, structures, or elements described above, as appropriate for the particular embodiment. As described above for the previous embodiments, the sealing element 604 may terminate at a tip section 606 through which a tip 608 of the hollow fluid delivery needle penetrates when the fluid reservoir 600 is engaged with the hollow fluid delivery needle 602 and with the sealing element 604 (see, for example, FIG. 12). For this particular embodiment, the tip section 606 is barbed or mushroom shaped such that it has a tapered convex exterior surface 610.

The fluid reservoir 600 generally includes, without limitation: a main body section 620; a filling port 621; a fluid delivery port 622; a funnel element 623; and a septum 624. The main body section defines a fluid chamber 626 for the medication fluid that is to be delivered by the fluid infusion device. The filling port 621 is in fluid communication with the fluid chamber 626 to accommodate filling of the fluid chamber 626 with the desired medication fluid (using a syringe or fill needle, as is well understood). The fluid delivery port 622 is coupled to, and extends from, the main body section 620. The fluid delivery port 622 is in fluid communication with the fluid chamber 626 to provide a fluid flow path from inside the fluid chamber 626 to the hollow fluid delivery needle 602 (this fluid flow path is established and maintained when the fluid reservoir 600 is engaged with the base plate of the fluid infusion device).

The funnel element 623 is coupled within the fluid delivery port 622. In certain embodiments, the main body section 620 and the fluid delivery port 622 are formed from a first material (such as plastic) and the funnel element 623 is formed from a second material (such as metal). The funnel element 623 may be implemented as an insert that can be seated within and coupled to the fluid delivery port 622 in any suitable manner such that the funnel element 623 remains in a fixed position. Notably, the funnel element 623 includes a tapered, conical, or convex interior surface 628. This interior surface 628 represents one surface of the receptacle that is defined by the funnel element 623. As schematically illustrated in FIG. 17, the funnel element 623 is shaped, sized, and configured in accordance with the sealing element 604. This enables the interior surface 628 of the funnel element 623 and the exterior surface 610 of the sealing element 604 to mate with one another and cooperate to form a fluid tight seal when they are forced together.

The septum 624 is located and held in place in the funnel element 623. The septum 624 may be formed from a soft, resilient, and pliable material that has certain self-sealing or self-restoring properties. For example, the septum 624 may be formed from a silicone rubber material in certain embodiments. Depending upon the embodiment, the septum 624 may be provided in a solid and continuous form, or it may be provided with a slit, a cut, or an equivalent feature that makes it easier to pierce while still maintaining at least a nominal seal. The septum 624 has a nominal non-pierced state (depicted in FIG. 17) where the needle does not protrude through the septum 624. In the non-pierced state, the septum 624 forms a fluid seal within a fluid conduit 630 defined by the fluid reservoir 600. Thus, the medication fluid inside the fluid chamber 626 cannot flow within the fluid conduit 630 when the fluid reservoir 600 is in the disengaged state shown in FIG. 17. However, when the fluid reservoir 600 is properly engaged with the hollow fluid delivery needle 602 and with the sealing element 604, the tip 608 of the hollow fluid delivery needle 602 penetrates the septum 624 to create a fluid flow path from the fluid chamber 626 through the septum 624. Accordingly, the hollow fluid delivery needle 602 pierces the septum 624 to facilitate delivery of the medication fluid from the fluid chamber to the hollow fluid delivery needle 602.

In various embodiments, the fluid delivery port 622 and/or the funnel element 623 include a pressure vent formed therein. The pressure vent may take any suitable form or arrangement. For example, the pressure vent may be realized with one or more vent holes. As another example, the pressure vent may be realized with one or more slits or any other opening formed within the funnel element 623. The exemplary embodiments shown in FIG. 17 and FIG. 18 employ small diameter vent holes 640 formed in the funnel element 623. As shown in FIG. 18, the vent holes 640 may be arranged around the perimeter of the fluid delivery port and/or around the perimeter of the funnel element 623. As depicted in FIG. 17, the vent holes 640 may be located around the outer perimeter of the septum 624. Thus, the vent holes 640 create venting conduits that pass around the septum 624 and pass around the fluid conduit 630. In practice, the vent holes 640 are sized to minimize leakage of the medication fluid caused by gravity or handling of the fluid reservoir 600. Of course, if the fluid chamber 626 is highly pressurized, then some medication fluid may be forced out of the vent holes 640 while the fluid chamber 626 equalizes.

Each vent hole 640 provides a venting conduit from inside the fluid chamber 626 to outside the fluid chamber 626. More specifically, each vent hole 640 is realized as a fluid conduit that communicates at one end with the fluid chamber 626 and at the other end with the interior surface 628 of the funnel element 623. Thus, each vent hole 640 terminates at the interior surface 628. When the fluid reservoir 600 is disengaged from the fluid infusion device, the vent holes 640 may be visible from the top of the fluid reservoir 600, as shown in FIG. 18.

In operation, the fluid delivery port 622 and the funnel element 623 engage and cooperate with the sealing element 604 and with the hollow fluid delivery needle 602 in the manner generally described above with reference to the fluid infusion device 100. When the fluid delivery port 622 is installed and pressed over the sealing element 604, the tip section 606 of the sealing element 604 is urged against the contoured interior surface 628 of the funnel element 623. This action causes the exterior surface 610 of the sealing element 604 to contact and mate with the interior surface 628 of the funnel element 623. In turn, the tip section 606 (which may deform or expand in response to the coupling) covers and seals the vent holes 640. As mentioned previously, the tip 608 of the hollow fluid delivery needle pierces the septum 624 when the fluid reservoir 600 is introduced. In certain embodiments, the fluid delivery port 622, the funnel element 623, the sealing element 604, and the hollow fluid delivery needle 602 are cooperatively configured such that the tip section 606 of the sealing element 604 seals the vent holes 640 before the hollow fluid delivery needle 602 pierces the septum 624. This reduces or eliminates leakage of the medication fluid. The vent holes 640 remain sealed in this manner during operation of the fluid infusion device, such that the medication fluid is forced from the fluid chamber 626 and through the hollow fluid delivery needle 602 in the intended manner.

Figure 19:
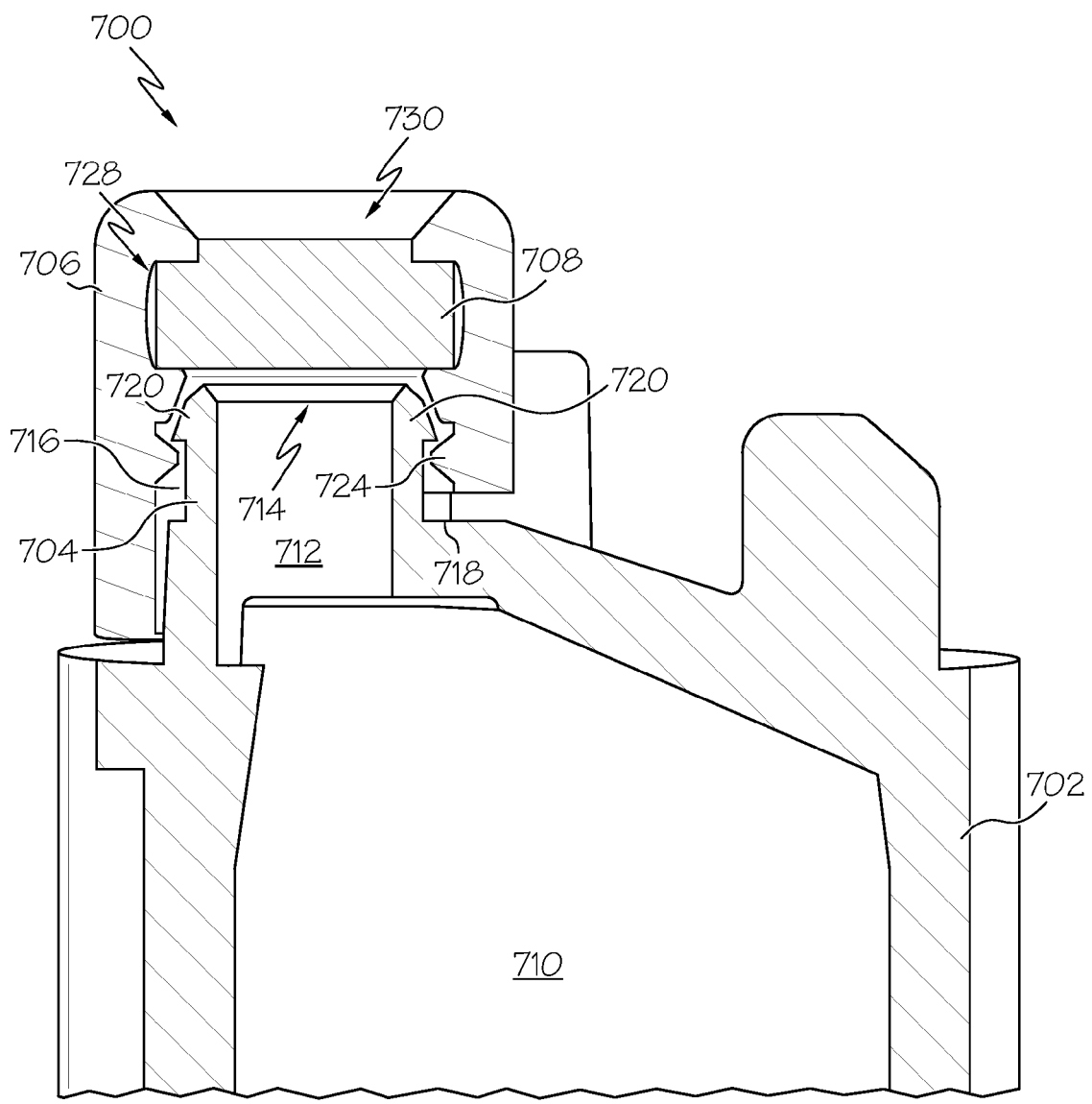
FIG. 19 is a phantom side view of an embodiment of a fluid reservoir that includes a septum that serves as a pressure relief valve.
Figure 20:
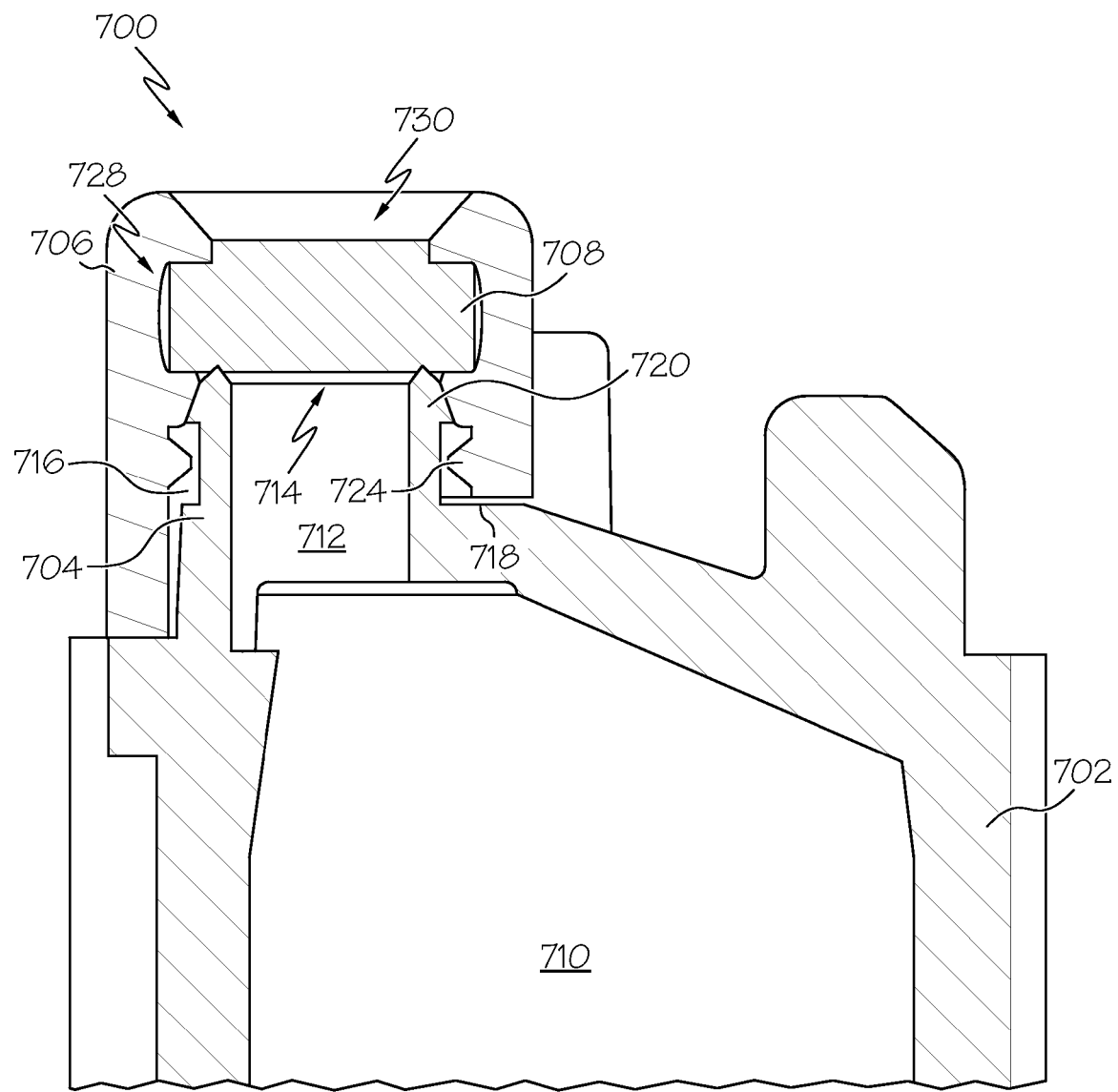
FIG. 20 is a phantom side view of the fluid reservoir shown in FIG. 19 in a sealed state.

Another embodiment of a vented fluid reservoir will now be described with reference to FIG. 19 and FIG. 20. FIG. 19 is a phantom side view of a fluid reservoir 700 in an open or vented state, and FIG. 20 is a phantom side view of the fluid reservoir 700 in a sealed state. It should be appreciated that the fluid reservoir 700 may be utilized with the fluid infusion device 100 (or a slightly modified version thereof) described above with reference to FIGS. 1-6. Accordingly, common features, structures, elements, and functionality will not be redundantly described here in the context of the fluid reservoir 700.

The illustrated embodiment of the fluid reservoir 700 generally includes, without limitation: a main body section 702; a fluid delivery port 704; a valve sleeve 706; and a septum 708. The main body section 702 includes a fluid chamber 710 defined therein. The fluid chamber 710 accommodates the medication fluid to be delivered to the patient. The fluid delivery port 704 is coupled to and extends from the main body section 702. In certain embodiments, the fluid delivery port 704 is integrally formed with the main body section 702. For example, the fluid delivery port 704 and the main body section 702 may be fabricated from a molded plastic material. The fluid delivery port 704 includes or defines a fluid conduit 712 that communicates with the fluid chamber 710.

This particular embodiment of the fluid delivery port 704 has a generally cylindrical shape that resembles a neck region extending from the main body section 702. The fluid delivery port 704 terminates at a port opening 714. The port opening 714 is realized as a round rim or lip at the end of the fluid delivery port 704. As shown in FIG. 19 and FIG. 20, the perimeter edge of the fluid delivery port 704 may be beveled or "pointed" if so desired (beveling in this manner may be desirable for purposes of creating a good seal with the septum 708).

Although not always required, the illustrated embodiment of the fluid delivery port 704 includes a circumferential groove 716 formed therein (around the outer surface). The groove 716 may be defined as a region between a shoulder 718 of the main body section 702 and a barb portion 720 of the fluid delivery port 704. For this embodiment, the barb portion 720 is located at or near the port opening 714. In alternative embodiments, the groove 716 could be positioned anywhere along the length of the fluid delivery port 704. The groove 716 receives an interior ridge 724 of the valve sleeve 706, which is formed within an attachment receptacle of the valve sleeve 706. This attachment receptacle is generally defined by the interior region below the septum 708 in FIG. 19 and FIG. 20. The attachment receptacle is shaped, sized, and otherwise configured to receive the fluid delivery port 704 as shown in the figures. The interior ridge 724 may be implemented as a continuous protrusion positioned within the attachment receptacle such that it completely encircles the fluid delivery port 704. The dimensions of the interior ridge 724 and the groove 716 are selected such that the valve sleeve 706 can be "snapped" into place and retained on the fluid delivery port 704 in a manner that accommodates translational movement of the valve sleeve 706 relative to the fluid delivery port 704.

Notably, the groove 716 allows the valve sleeve 706 to move toward the fluid chamber 710 until movement is inhibited by the shoulder 718 and/or by other structure of the fluid reservoir 700, or until movement is inhibited by engagement between the septum 708 and the port opening 714 (see FIG. 20). Similarly, the groove 716 allows the valve sleeve 706 to move away from the fluid chamber 710 until movement of the interior ridge 724 is inhibited by the barb portion 720 of the fluid delivery port 704 (see FIG. 19). Thus, the valve sleeve 706 is movably coupled to the fluid delivery port 704, and the attachment receptacle of the valve sleeve 706 is sized to accommodate translation of the valve sleeve 706 relative to the fluid delivery port 704 and, more particularly, relative to the port opening 714.

The septum 708 is located within a septum receptacle 728 defined within the valve sleeve 706. The septum receptacle 728 may be realized as an interior groove or channel formed in the inner wall of the valve sleeve 706. In the illustrated embodiment, the septum receptacle 728 is adjacent to the attachment receptacle, such that one surface of the septum 708 (i.e., the lower surface in FIG. 19 and FIG. 20) defines a boundary of the attachment receptacle. The septum receptacle 728 receives and holds the septum 708 in a fixed position relative to the valve sleeve 706. In other words, the septum receptacle 728 maintains the septum 708 in place such that the septum 708 translates in concert with the valve sleeve 706. In this regard, the septum 708 is movably coupled to the fluid delivery port 704 by way of the valve sleeve 706.

The valve sleeve 706 also includes a sleeve opening 730 that is adjacent to the septum receptacle 728. The sleeve opening 730 is arranged such that at least a portion of the septum 708 is accessible via the sleeve opening 730. As shown in FIG. 19 and FIG. 20, the upper surface of the septum 708 is exposed in the sleeve opening 730. The sleeve opening 730 allows a hollow fluid delivery needle of the fluid infusion device to pierce or otherwise pass through the septum 708 to gain entry to the fluid conduit 712.

The valve sleeve 706 and the septum 708 are movable between a sealed position (shown in FIG. 20) and an open or vented position (shown in FIG. 19). The sealed position is achieved when the fluid reservoir 700 is engaged with the fluid delivery needle of the fluid infusion device. More specifically, the septum 708 and the valve sleeve 706 are urged into the sealed position when the fluid delivery needle is forced against and through the septum 708. Additionally or alternatively, the septum 708 could be urged into the sealed position when the valve sleeve 706 abuts structure of the base plate. When in the sealed position, the surface of the septum 708 contacts the port opening 714 to form a circumferential seal around the port opening 714. This seal inhibits fluid flow between the fluid delivery port 704 and the septum 708 during a delivery cycle (which is intended to force the medication fluid through the delivery needle). For simplicity, the needle and its associated base plate mounting structure are not shown in FIG. 20.

When the fluid reservoir 700 is removed from the fluid infusion device and, therefore, is disengaged from the fluid delivery needle, the valve sleeve 706 and the septum 708 are free to move relative to the fluid delivery port 704. Accordingly, the valve sleeve 706 and the septum 708 are free to move into the vented position in response to a pressure differential condition where pressure in the fluid chamber 710 exceeds the ambient pressure. Under these conditions, the excess pressure inside the fluid chamber 710 can be released through the port opening 714 because the valve sleeve 706 and the septum 708 function as a pressure relief valve. When subjected to excess pressure in this manner, the septum 708 moves slightly upward, which creates a gap between the bottom surface of the septum 708 and the port opening 714. Consequently, the septum 708 permits fluid to flow out of the fluid delivery port 704 via the port opening 714 when the valve sleeve 706 is in the vented position. After the pressure is equalized, however, the valve sleeve 706 and the septum 708 might naturally return to the sealed position shown in FIG. 20, especially if the fluid reservoir 700 is held in the depicted orientation (where the force of gravity may cause the valve sleeve 706 to fall into the sealed position).

Needleless Fluid Reservoir Interface

The embodiments described above utilize a hollow needle that engages the fluid reservoir during operation of the fluid infusion device. An alternative needleless implementation will now be described with reference to FIG. 21 and FIG. 22. FIG. 21 is a longitudinal cross-sectional view of a fluid reservoir 800 and a self-sealing reservoir port receptacle 802 suitable for use with a fluid infusion device, and FIG. 22 is an end view of the fluid reservoir 800 as viewed from the perspective of line 22-22 in FIG. 21. The fluid reservoir 800 and the self-sealing reservoir port receptacle 802 may be utilized with the fluid infusion device 100 (or a slightly modified version thereof) described above with reference to FIGS. 1-6. Accordingly, common features, structures, elements, and functionality will not be redundantly described here in the context of the fluid reservoir 800 and the self-sealing reservoir port receptacle 802.

The fluid reservoir 800 may be intended to be a user-filled or refillable unit, or it could be designed to be a disposable pre-filled unit, depending upon the particular application. The fluid reservoir 800 includes a main body section 804 that defines an interior fluid chamber 806 for holding the desired fluid, e.g., a medication fluid such as insulin. The fluid reservoir 800 also includes a fluid delivery port 808 that is coupled to, and extends from, the main body section 804. The fluid delivery port 808 includes or otherwise defines a fluid conduit 810 that communicates with the fluid chamber 806. The fluid conduit 810 is used to deliver the fluid from the fluid chamber 806. In certain embodiments, the fluid conduit 810 may also be used as the fill port of the fluid reservoir 800.

Notably, the fluid reservoir 800 is "unsealed" in that the fluid delivery port 808 terminates at an unsealed port opening 812. In this regard, the fluid delivery port 808 does not include a septum or any equivalent form of fluid seal that remains in place during use of the fluid infusion device. That said, the fluid reservoir 800 could be manufactured and provided with a protective seal or film that is removed prior to use. For instance, a prefilled version of the fluid reservoir 800 may include a temporary cover, lid, or cap that can be removed prior to use. In the context of a user-filled unit, the unsealed nature of the fluid reservoir 800 allows the fluid chamber 806 to be filled in a manner that inherently equalizes the pressure. Consequently, the fluid chamber 806 will not be over-pressurized when the fluid reservoir 800 is introduced to the fluid infusion device.

The fluid delivery port 808 and the port opening 812 are shaped and sized in accordance with the dimensions of the self-sealing reservoir port receptacle 802. More specifically, the fluid delivery port 808 and the port opening 812 are shaped and dimensioned to facilitate mating and engagement with the self-sealing reservoir port receptacle 802. In this regard, the fluid delivery port 808 is inserted into the self-sealing reservoir port receptacle 802 to enable the fluid reservoir 800 to provide the medication fluid to the body of the patient via the self-sealing reservoir port receptacle 802.

In certain embodiments, the port opening 812 includes at least one flow path 814 (see FIG. 22) that allows the medication fluid to flow from the fluid conduit 810 and into the self-sealing reservoir port receptacle 802 when the fluid reservoir 800 is engaged with and coupled to the self-sealing reservoir port receptacle 802. The illustrated embodiment employs five channels formed in the exposed rim 816 of the fluid delivery port 808. The fluid is able to flow through these channels during a delivery cycle of the fluid infusion device (as described in more detail below). In alternative embodiments, the at least one flow path 814 may be realized as through holes, slits, or any suitably configured conduit to pass the medication fluid. Moreover, the port opening 812 could be shaped (e.g., to resemble a crown) in any desired way to enable the medication fluid to flow from the fluid conduit 810 during use.

In various embodiments, the self-sealing reservoir port receptacle 802 is coupled to, provided with, or incorporated into a base plate of the fluid infusion device (see, for example, a similar arrangement depicted in FIG. 1 and FIG. 3). As mentioned previously, the fluid infusion device may include a suitable delivery conduit, such as the cannula 112 shown in FIG. 1, wherein the delivery conduit provides the medication fluid to the body. Accordingly, the self-sealing reservoir port receptacle 802 may be located on the base plate to establish a flow path for the medication fluid from the fluid reservoir 800 to the delivery conduit.

The illustrated embodiment of the self-sealing reservoir port receptacle 802 is implemented as a needleless component. In other words, a delivery needle is not utilized with either the self-sealing reservoir port receptacle 802 or the fluid reservoir 800. Rather, the self-sealing reservoir port receptacle 802 incorporates a biased valve element 830 that is nominally closed in its natural state, but is opened in response to engagement of the fluid reservoir 800. Referring to FIG. 21, the exemplary embodiment of the self-sealing reservoir port receptacle 802 generally includes, without limitation: an inlet 832; a valve chamber 834 for the valve element 830; and an outlet 836. For this particular embodiment, the inlet 832, the valve chamber 834, and the outlet 836 are joined together to define a continuous hollow interior pathway.

The inlet 832 is suitably configured, shaped, and sized to receive the fluid delivery port 808 of the fluid reservoir 800. For this embodiment, the inlet 832 includes an interior 838 that is sized to receive the fluid delivery port 808. In alternative embodiments, the inlet 832 may be sized to fit inside the fluid conduit 810. The inlet 832 may also include or cooperate with a sealing element 840 that forms a seal with the outer surface of the fluid delivery port 808 when the fluid delivery port 808 is engaged with the inlet 832. In various embodiments, the sealing element 840 is realized as a resilient gasket, o-ring, washer, or the like. Moreover, although the depicted embodiment has the sealing element 840 incorporated into the inlet 832, the sealing element 840 may alternatively (or additionally) be incorporated into the fluid delivery port 808. When the fluid delivery port 808 is engaged with the inlet 832, the sealing element 840 inhibits leakage of fluid from the port opening 812 and from the valve chamber 834.

The valve chamber 834 is in fluid communication with the inlet 832. For this particular embodiment, the downstream end of the inlet 832 corresponds to the upstream end of the valve chamber 834, as shown in FIG. 21. The valve chamber 834 is shaped, sized, and otherwise configured to retain the valve element 830 while allowing the valve element 830 to translate in the upstream and downstream directions within the valve chamber 834. The upstream end of the valve chamber 834 may include a retaining shoulder 844 formed therein. The retaining shoulder 844 may be defined as the transition from a relatively small inner dimension corresponding to the inlet 832 to a relatively large inner dimension corresponding to the valve chamber 834. In other words, the retaining shoulder 844 represents a neck region that prevents the valve element 830 from completely entering the inlet 832.

The self-sealing reservoir port receptacle 802 also includes a resilient compression element 846 located in the valve chamber 834. The resilient compression element 846 can be positioned between the valve element 830 and the downstream end of the valve chamber 834. The resilient compression element 846 is sized and configured to bias the valve element 830 toward the inlet 832 (as shown in FIG. 21). In other words, the resilient compression element 846 naturally urges the valve element 830 against the retaining shoulder 844 and into a sealed position to form a fluid seal between the valve element 830 and the inlet 832. In certain embodiments, the resilient compression element 846 is realized as a spring. Alternatively, the resilient compression element 846 could be realized as a compressible plug, an accordion-like member, or the like.

The valve element 830 may be shaped and sized as appropriate for the particular embodiment. FIG. 21 depicts one exemplary embodiment where the valve element 830 is realized as a ball valve, i.e., the valve element 830 includes a spherical component. Thus, the valve chamber 834 may be fabricated as a cylindrical cavity to accommodate the round profile of the valve element 830. Alternatively, the valve element 830 could be realized as a cylindrical plug. Various shapes and configurations could be utilized for the valve element 830, and the ball valve implementation is merely one suitable embodiment.

The downstream end of the valve chamber 834 is in fluid communication with the outlet 836 such that medication fluid can pass through the valve chamber 834 and into the outlet 836. The outlet 836 provides a fluid flow path 848 for the medication fluid. In this regard, the fluid flow path 848 may be routed through the base plate and/or through other structure of the fluid infusion device, and to the delivery conduit that leads to the body of the user, as described previously. In other words, the outlet 836 can be positioned between the valve chamber 834 and the delivery conduit.

FIG. 21 shows the self-sealing reservoir port receptacle 802 in its sealed position. The sealed state is automatically assumed in the absence of the fluid reservoir 800. In other words, when the fluid delivery port 808 is disengaged from the inlet 832 of the self-sealing reservoir port receptacle 802, the resilient compression element 846 forces the valve element 830 toward the inlet 832 and against the retaining shoulder 844, which in turn forms a fluid seal between the valve element 830 and the inlet 832. This seal is desirable to prevent backflow leakage of the medication fluid and to reduce the likelihood of contamination of the fluid path.

Engagement of the fluid delivery port 808 with the inlet 832 causes the end of the fluid delivery port 808 to contact the valve element 830. Further engagement and complete coupling of the fluid delivery port 808 within the inlet 832 causes the end of the fluid delivery port 808 to move the valve element 830 from the sealed position (shown in FIG. 21) to an opened position. In the opened position, the valve element 830 is forced in the downstream direction toward the outlet 836. As a result of this movement, the resilient compression element 846 becomes compressed and compacted within the valve chamber 834. Refraction of the valve element 830 in this manner also enables the fluid delivery port 808 to gain access to the valve chamber 834, which in turn accommodates flow of the medication fluid from the fluid reservoir 800 and into the valve chamber 834. Referring again to FIG. 22, the at least one flow path 814 in the exposed rim 816 ensures that the medication fluid can flow into the valve chamber 834 (even though the end of the fluid delivery port 808 is in contact with the valve element 830).

Needled Fluid Reservoir for a Fluid Infusion Device

Most of the embodiments described previously employ a hollow fluid delivery needle that is provided with a base plate of a fluid infusion device (see, for example, FIGS. 1-5). The needle in such embodiments cooperates with a sealed or an open fluid reservoir, wherein the needle is introduced into the fluid chamber of the fluid reservoir to accommodate delivery of the medication fluid from the fluid chamber, through the needle, and to the body of the patient.

Alternatively, the embodiments presented in this section utilize a needled fluid reservoir, i.e., a fluid reservoir having a hollow fluid delivery needle incorporated therein. The hollow needle engages a suitably configured reservoir port receptacle, which may be located on the base plate of the fluid infusion device. The reservoir port receptacle includes a fluid conduit that is used to deliver the medication fluid to the body of the patient. In certain embodiments, the reservoir needle is unsealed and, therefore, open to ambient pressure. Accordingly, the fluid infusion device includes an appropriate sealing arrangement to establish a fluid seal with the hollow needle when the fluid reservoir is engaged with the reservoir port receptacle.

Figure 23:
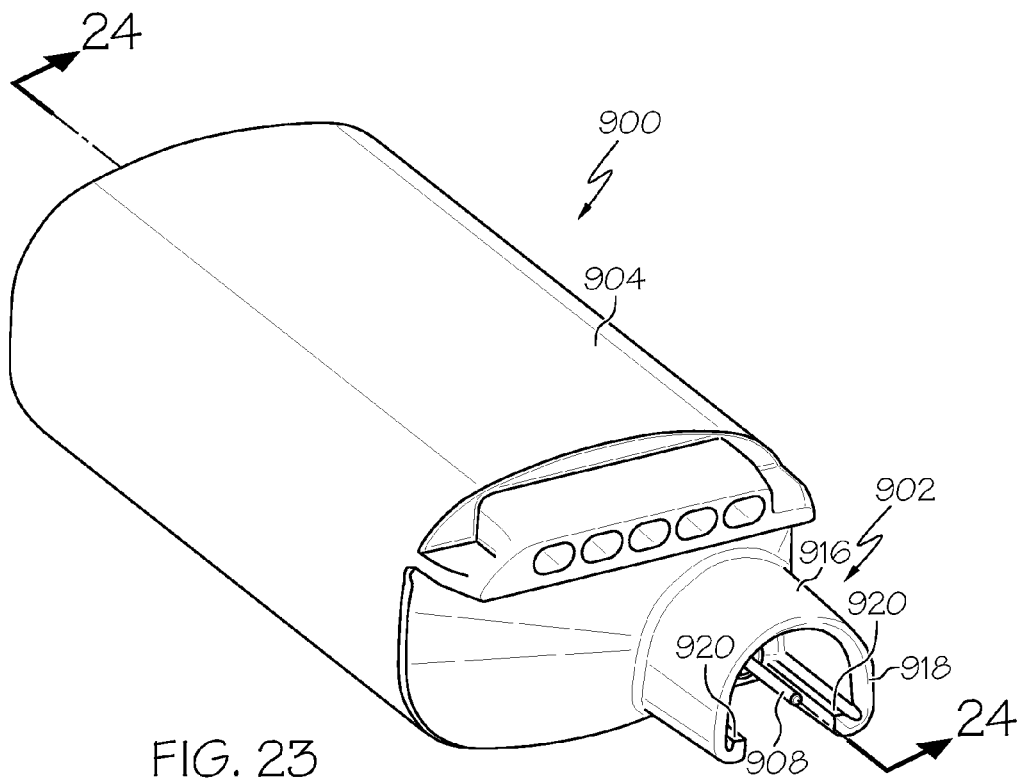
FIG. 23 is a perspective view of a first embodiment of a fluid reservoir that includes a needle.
Figure 24:
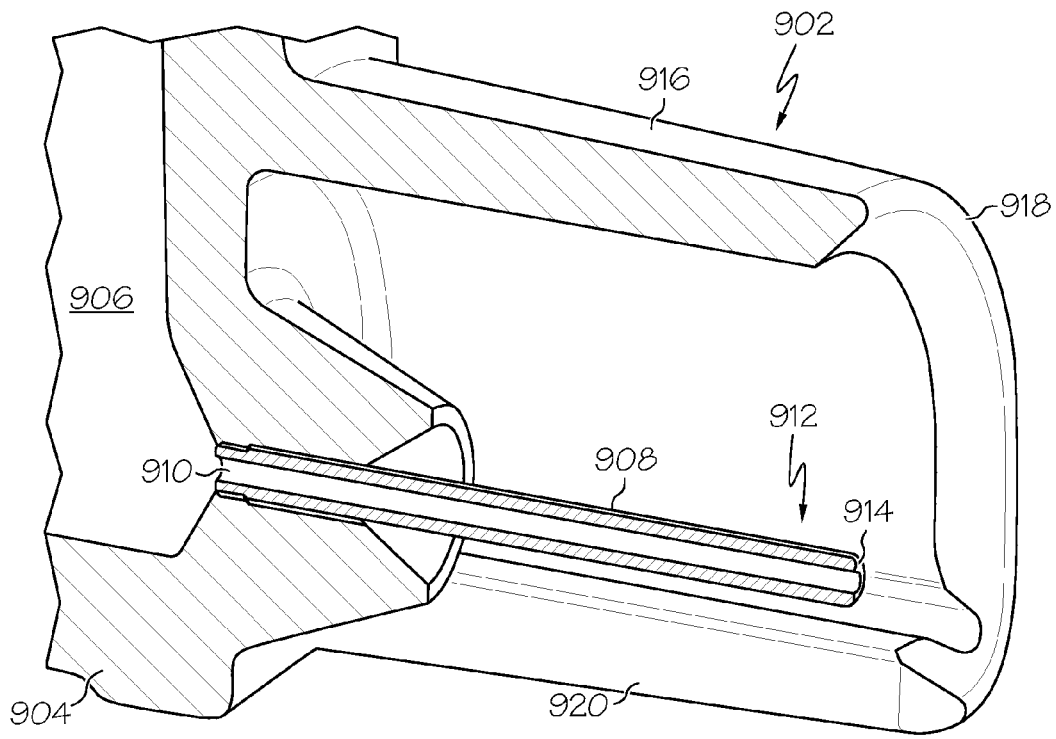
FIG. 24 is a cross-sectional view of a portion of the fluid reservoir, as viewed from the perspective of line 24-24 in FIG. 23.

FIGS. 23-29 relate to a first embodiment of a needled fluid reservoir 900 that is suitable for use with a compatible fluid infusion device. FIG. 23 is a perspective view of the fluid reservoir 900, and FIG. 24 is a cross-sectional view of an end portion 902 of the fluid reservoir 900. It should be appreciated that the fluid reservoir 900 could be utilized with a modified version of the fluid infusion device 100 described above with reference to FIGS. 1-6. Accordingly, common features, structures, elements, and functionality will not be redundantly described here with reference to FIGS. 23-29. Moreover, the fluid reservoir 900 shares a number of features and elements with some of the fluid reservoirs described previously. For the sake of brevity, such common features and elements will not be described in detail again in the context of the fluid reservoir 900.

Referring to FIG. 23 and FIG. 24, the fluid reservoir 900 includes a main body section 904 that defines an interior fluid chamber 906 for a fluid to be delivered, such as a medication fluid. The fluid reservoir 900 also includes a hollow needle 908 extending from the main body section 904 and defining a fluid conduit 910 (see FIG. 24) that communicates with the fluid chamber 906. Although not always required, the illustrated embodiment of the hollow needle 908 is realized as a separate component that is physically coupled to the main body section 904 (and/or to a structural feature defined in the main body section 904) in an appropriate manner to communicate with the fluid chamber 906. In this regard, the hollow needle 908 and the main body section 904 in this particular embodiment are realized as two physically distinct and separate components that are assembled together into the configuration shown in the figures. For example, the main body section 904 could be fabricated from a molded plastic material, and the hollow needle 908 could be fabricated from a metal material, as appropriate to the specific embodiment. In practice, the hollow needle 908 is coupled to the main body section 904 in a way that prevents leakage of fluid between the main body section 904 and the outer surface of the hollow needle 908.

As best shown in FIG. 24, the hollow needle 908 terminates at a needle end 912 that forms or otherwise defines a blunt tip 914. The blunt tip 914 may be flat (as shown), rounded, mushroom-shaped, or otherwise contoured in a way that does not result in a sharp or pointed needle end 912. Moreover, the hollow needle 908 may be unsealed such that the fluid conduit 910 remains open to ambient or atmospheric pressure, which is desirable to enable the fluid reservoir 900 to equalize its internal pressure inside the fluid chamber 906 via the hollow needle 908. The fluid conduit 910 is preferably sized to inhibit or prevent natural leakage of the fluid, while still accommodating the delivery of the medication fluid from the fluid chamber 906. Moreover, for embodiments where the hollow needle 908 also serves as the fill needle, the fluid conduit 910 is sized to enable quick and easy filling of the fluid reservoir 900. As described in more detail below, the blunt tip 914 is suitably sized, shaped, and configured to engage a sealing element of the fluid infusion device.

Various embodiments of the fluid reservoir 900 include a needle hood 916 that at least partially covers the hollow needle 908. The needle hood 916 extends from the main body section 904 to at least partially surround the hollow needle 908, while still providing access to the hollow needle 908 from the end, as best shown in FIG. 23. As depicted in FIG. 24, the illustrated embodiment of the needle hood 916 is integrated with the main body section 904. Thus, the needle hood 916 can be molded together with the main body section 904 as a unitary component. The needle hood 916 terminates at a lip 918. In certain embodiments, the lip 918 extends further from the main body section 904 than the needle end 912. In other words, the blunt tip 914 of the hollow needle 908 does not protrude from the lip 918 (see FIG. 24). This arrangement is desirable to protect the hollow needle 908 from damage and contamination. This arrangement also protects the user if the hollow needle 908 is provided with a sharp tip.

Figure 25:
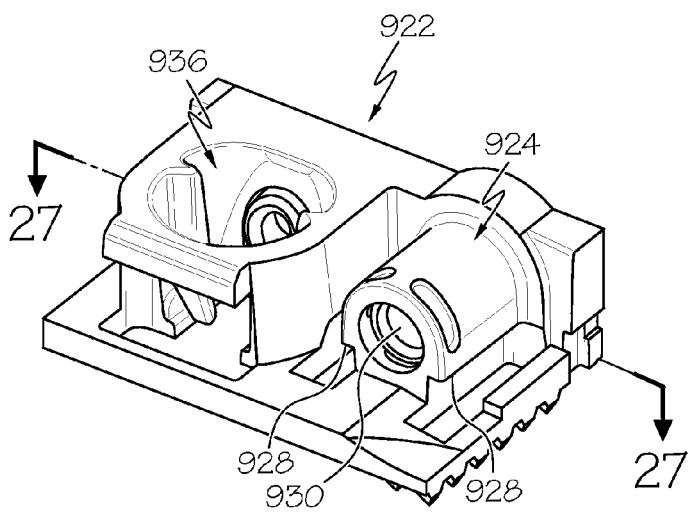
FIG. 25 is a perspective view of a section of a fluid infusion device, including a reservoir port receptacle suitable for engagement with the fluid reservoir shown in FIG. 23.

The fluid reservoir 900 may also include an alignment structure that mates with cooperating structure of the reservoir port receptacle of the fluid infusion device (see FIG. 25 and related description). Although not always required, at least a portion of the alignment structure may be integrally formed with the needle hood 916. For example, the illustrated embodiment of the fluid reservoir 900 utilizes opposing guide rails 920 and a particular shape for the needle hood 916 (e.g., an inverted "U" shape when viewed from the perspective of FIG. 23) that cooperate to provide the desired alignment features. The guide rails 920 and the shape of the needle hood 916 have corresponding mating features on the reservoir port receptacle shown in FIG. 25.

Figure 26:
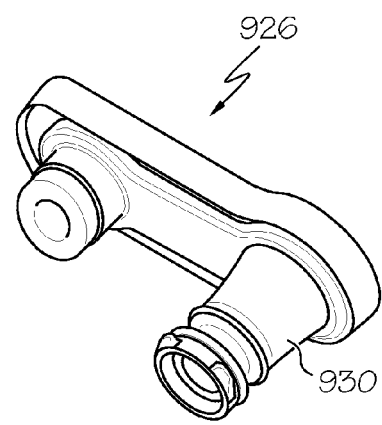
FIG. 26 is a perspective view of a sealing and conduit component suitable for use with the fluid infusion device shown in FIG. 25.

FIG. 25 is a perspective view of a section 922 of a fluid infusion device, including a reservoir port receptacle 924 suitable for engagement with the fluid reservoir 900. The section 922 may represent a portion of a base plate of the fluid infusion device (see FIGS. 3-6, which show the base plate 104 with a similarly configured section for the fluid infusion device 100). FIG. 26 is a perspective view of a sealing and conduit component 926 suitable for use in the section 922 shown in FIG. 25, and FIG. 27 is a cross-sectional view of the section 922, as viewed from the perspective of line 27-27 in FIG. 25.

The reservoir port receptacle 924 includes suitably designed mating structure 928 that is intended to engage and mate with the needle hood 916 and, more particularly, to engage with the alignment structure of the needle hood 916. For this particular embodiment, the mating structure 928 is realized as two shoulders or channels that cooperate with the guide rails 920 when the fluid reservoir 900 is coupled to the reservoir port receptacle 924. Moreover, the overall outer shape and contour of the reservoir port receptacle 924 can be shaped and sized to match the interior space defined by the needle hood 916. These features cooperate to orient, align, and guide the needle hood 916 over the reservoir port receptacle 924. Accordingly, the alignment structure of the fluid reservoir 900 cooperates with the mating structure 928 to align and orient the hollow needle 908 relative to the reservoir port receptacle 924. This facilitates proper introduction and insertion of the hollow needle 908 into a sealing element 930 of the reservoir port receptacle 924.

Figure 27:
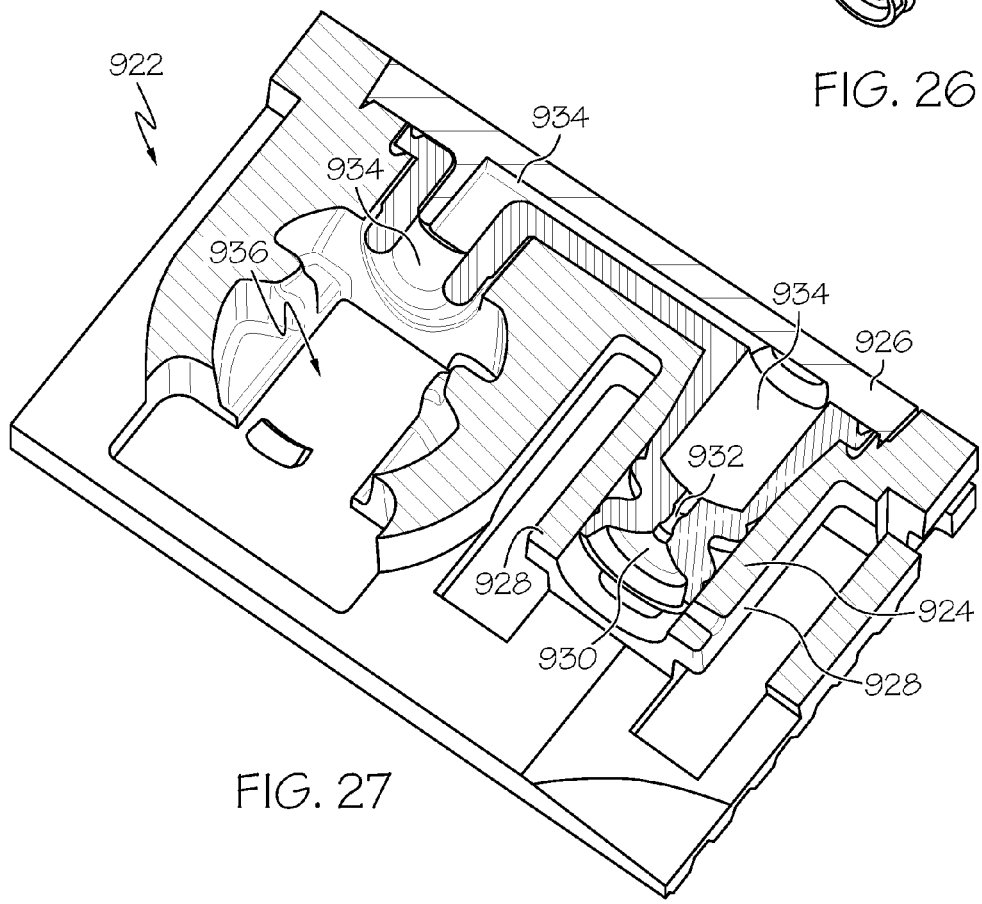
FIG. 27 is a cross-sectional view of the section of the fluid infusion device, as viewed from the perspective of line 27-27 in FIG. 25.

The sealing and conduit component 926 may be realized as an insert or a plug that is received within the section 922, as shown in FIG. 27. The sealing element 930 may be coupled to or integrally formed with the sealing and conduit component 926, as shown in FIG. 26 and FIG. 27. The embodiment of the sealing element 930 shown in FIG. 27 includes a self-sealing opening 932 to receive the hollow needle 908. Notably, the self-sealing opening 932 is particularly suitable for use with the blunt tip 914, which is not designed to pierce or puncture the sealing element 930. Rather, the blunt tip 914 can pass through the self-sealing opening 932 when the fluid reservoir 900 is urged into the reservoir port receptacle 924 (as depicted in FIG. 29).

Figure 28:
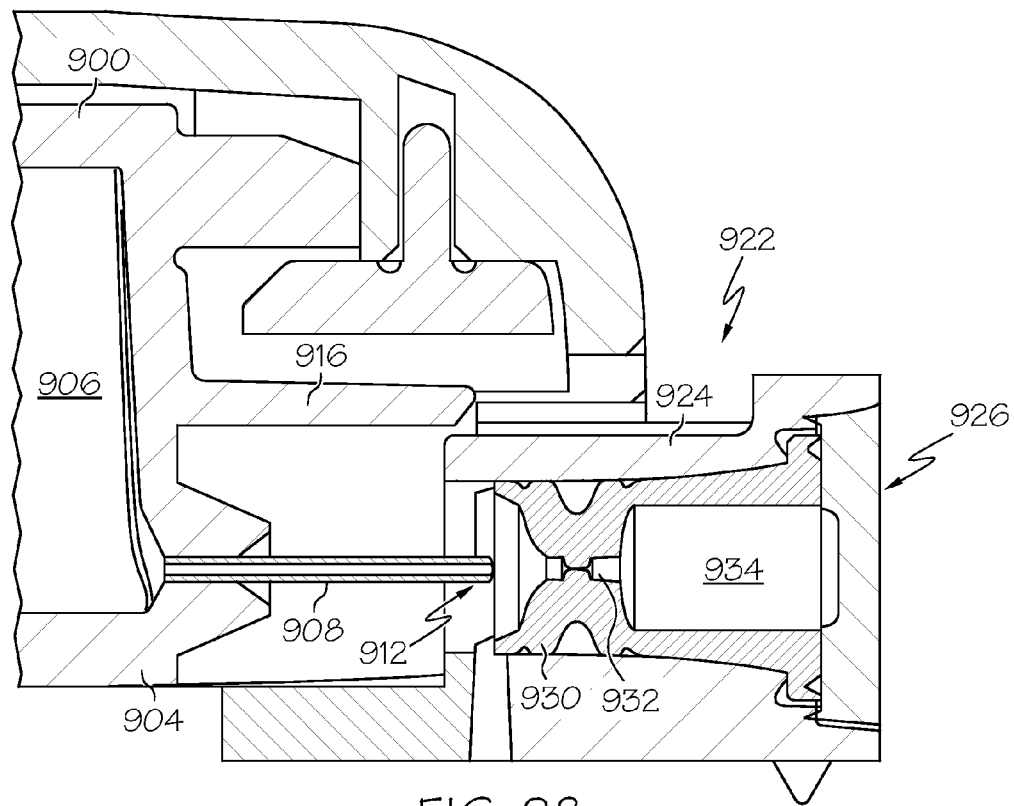
FIG. 28 is a cross-sectional and partially phantom view that illustrates the fluid reservoir (shown in FIG. 23) before engagement with the section of the fluid infusion device (shown in FIG. 25)
Figure 29:
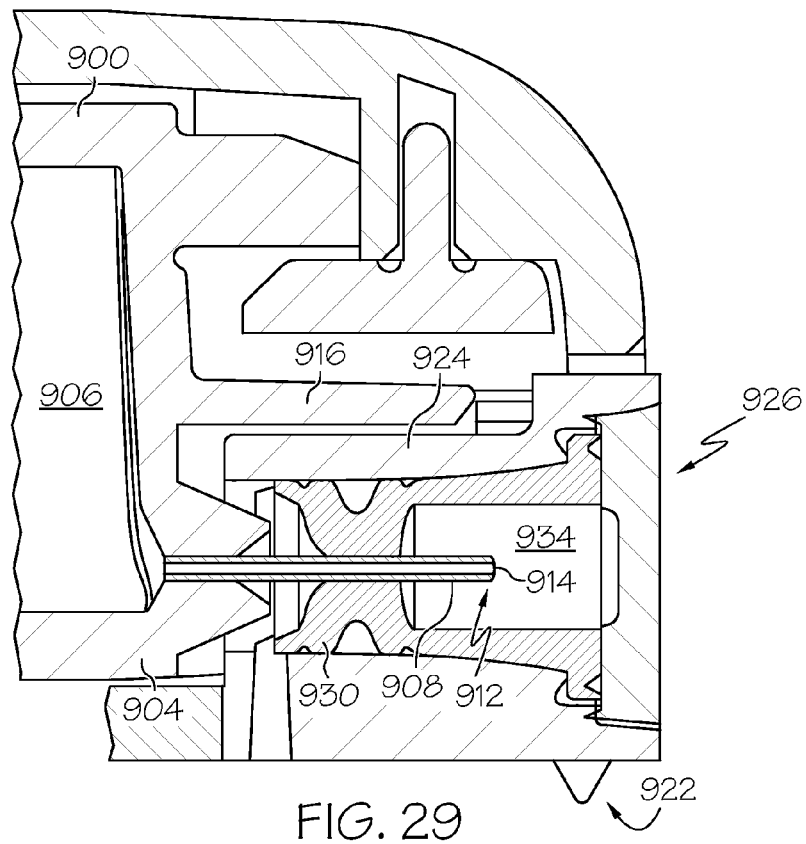
FIG. 29 is a cross-sectional and partially phantom view that illustrates the fluid reservoir (shown in FIG. 23) after engagement with the section of the fluid infusion device (shown in FIG. 25)
Figure 30:
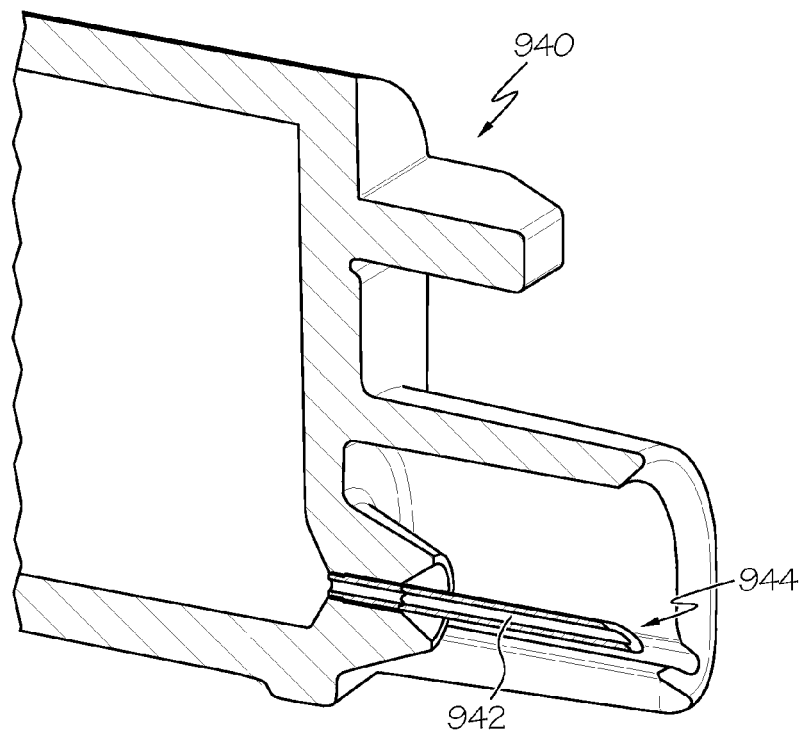
FIG. 30 is a cross-sectional view of a portion of a second embodiment of a needled fluid reservoir.

FIG. 28 is a cross-sectional and partially phantom view that illustrates the fluid reservoir 900 before engagement with the section 922 of the fluid infusion device, and FIG. 29 is a cross-sectional and partially phantom view that illustrates the fluid reservoir 900 after engagement with the section 922. In FIG. 28, the needle end 912 has not yet contacted the sealing element 930. Accordingly, the self-sealing opening 932 exhibits a sealed or compressed state to prevent fluid ingress into an outlet conduit 934 of the reservoir port receptacle 924. In FIG. 29, however, engagement of the fluid reservoir 900 with the reservoir port receptacle 924 causes the blunt tip 914 to penetrate the self-sealing opening 932 such that the needle end 912 resides within the outlet conduit 934. Accordingly, fluid communication is established from the fluid chamber 906 to the outlet conduit 934, via the hollow needle 908. In this state, the sealing element 930 forms a seal around the exterior surface of the hollow needle 908 to inhibit fluid leakage from the outlet conduit 934.

As shown in FIGS. 27-29, the outlet conduit 934 may be at least partially defined by the sealing element 930. For this particular embodiment, the outlet conduit 934 is integrally formed within the sealing and conduit component 926 to provide a fluid flow path from the self-sealing opening 932, across a span of the section 922 (see FIG. 27) and into a fluid chamber 936 defined in the base plate. The fluid chamber 936 may be fluidly coupled to a delivery conduit such as a cannula (see FIG. 1, which shows the cannula 112 for the fluid infusion device 100) for purposes of fluid delivery to the body of the patient. Thus, the sealing and conduit component 926 may be employed instead of a "J" shaped hollow needle as described above with reference to FIG. 6.

It should be appreciated that the needle hood 916 and/or the alignment structure of the fluid reservoir 900 may also be designed to mate and cooperate with corresponding structure of a reservoir filling apparatus. In this regard, the alignment structure could also serve to align and orient the hollow needle 908 relative to the reservoir filling apparatus to facilitate insertion of the hollow needle 908 into a sealing element or entry port of the reservoir filling apparatus. This dual-purpose nature of the needle hood 916 and alignment structure may be desirable for embodiments of the fluid reservoir 900 that use the same hollow needle 908 for both filling and delivery of the medication fluid.

FIGS. 30-33 relate to a second embodiment of a needled fluid reservoir 940 that is suitable for use with a compatible fluid infusion device. The fluid reservoir 940 and the related features of the fluid infusion device are similar in many respects to that described above for the fluid reservoir 900. Accordingly, for the sake of brevity and clarity, the following description referring to FIGS. 30-33 is abbreviated in nature.

Figure 31:
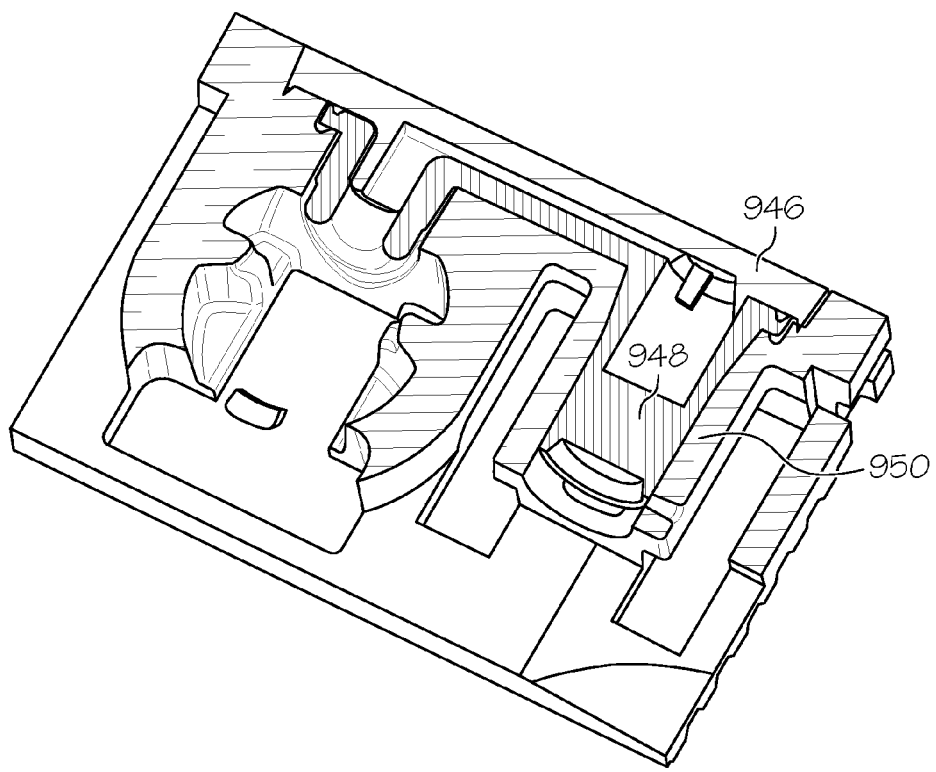
FIG. 31 is a cross-sectional view of a section of a fluid infusion device that is designed to accommodate the needled fluid reservoir shown in FIG. 30.

The fluid reservoir 940 is very similar to the fluid reservoir 900, except for its use of a hollow needle 942 terminating at a sharp tip 944 (rather than a blunt or rounded tip). Likewise, the sealing and conduit component 946 shown in FIG. 31 is substantially identical to the sealing and conduit component 926 described above. Notably, however, the sealing and conduit component 946 includes a pierceable sealing element 948 (rather than a self-sealing element having a predefined slit, hole, or slot formed therein) that is suitably configured to accommodate the sharp tip 944. Thus, the sharp tip 944 pierces the sealing element 948 when the fluid reservoir 940 is coupled to the reservoir port receptacle 950.

Figure 32:
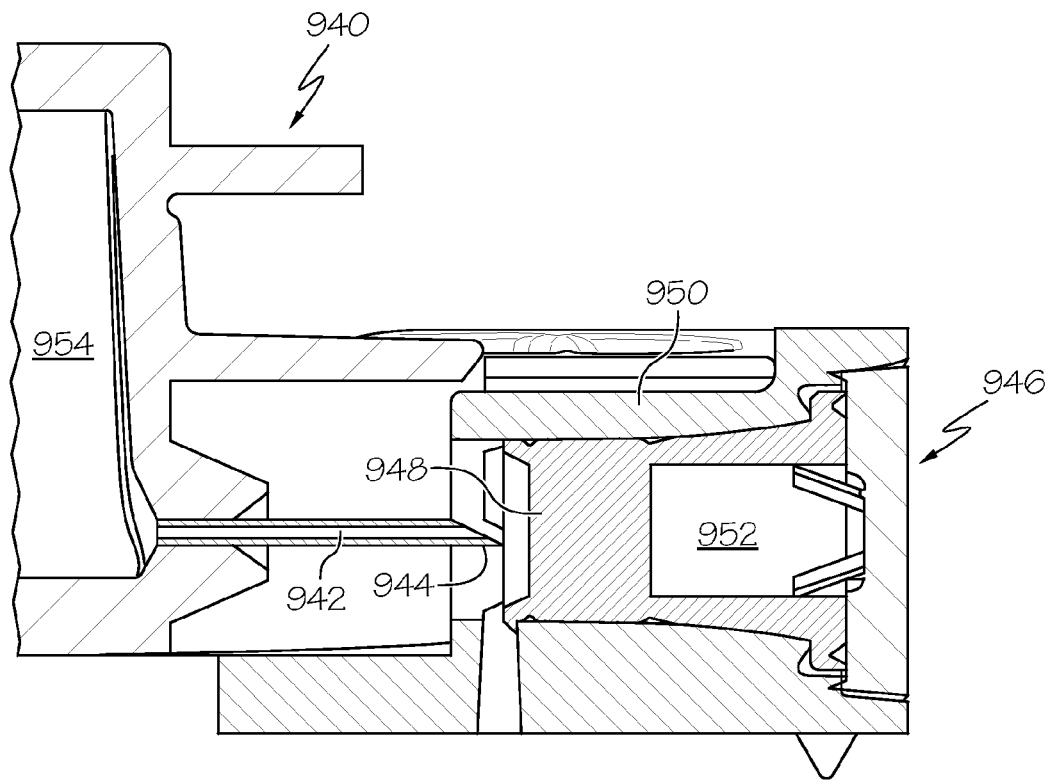
FIG. 32 is a cross-sectional and partially phantom view that illustrates the fluid reservoir (shown in FIG. 30) before engagement with the section of the fluid infusion device (shown in FIG. 31)
Figure 33:
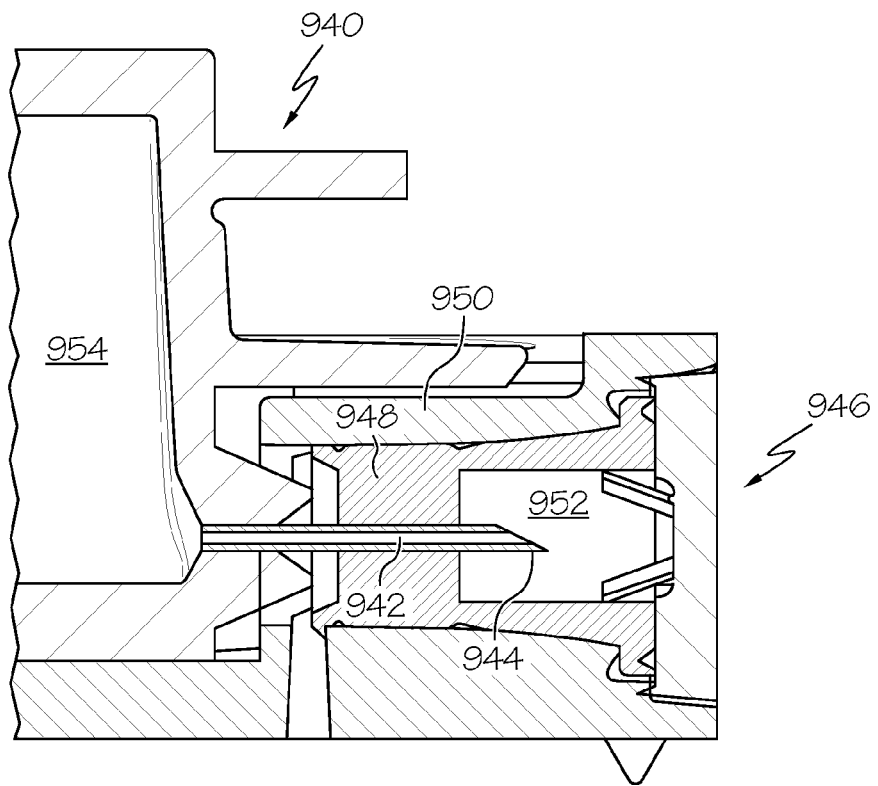
FIG. 33 is a cross-sectional and partially phantom view that illustrates the fluid reservoir (shown in FIG. 30) after engagement with the section of the fluid infusion device (shown in FIG. 31)
Figure 34:
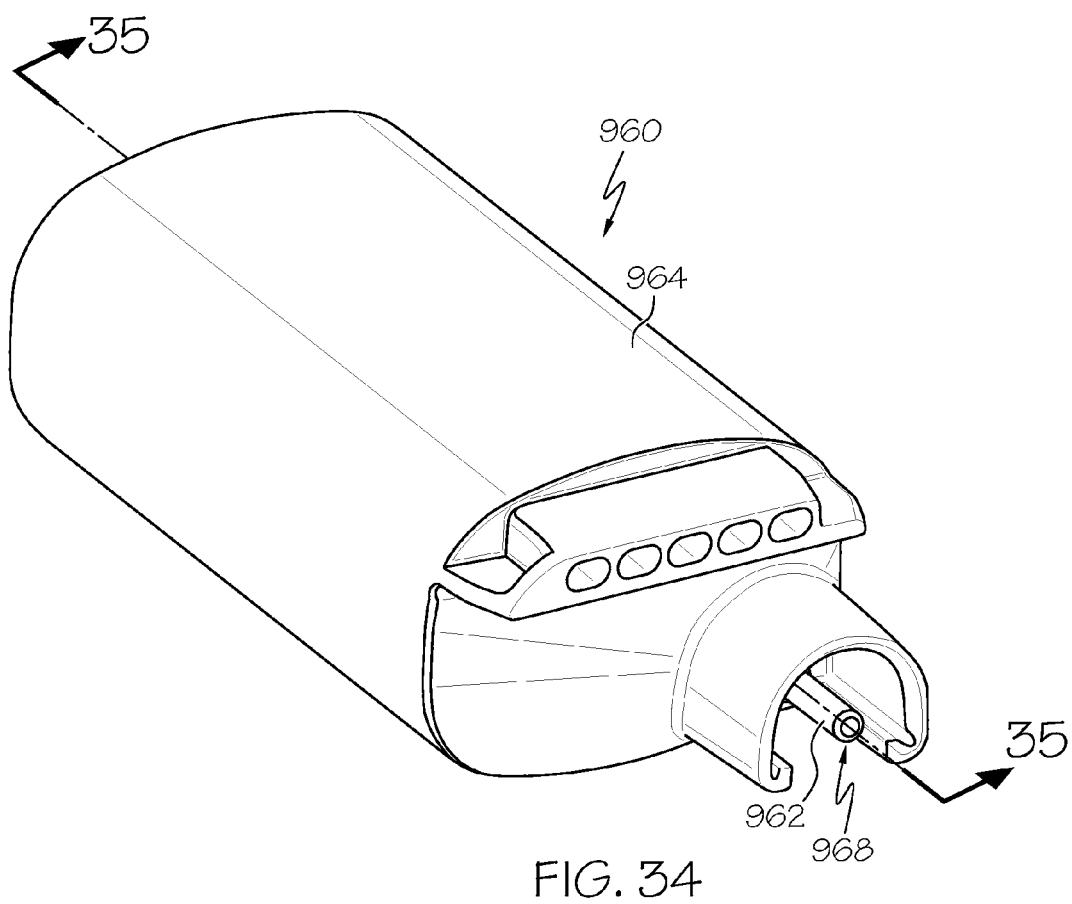
FIG. 34 is a perspective view of a third embodiment of a needled fluid reservoir.

FIG. 32 is a cross-sectional and partially phantom view that illustrates the fluid reservoir 940 before engagement with the reservoir port receptacle 950, and FIG. 33 is a cross-sectional and partially phantom view that illustrates the fluid reservoir 940 after engagement with the reservoir port receptacle 950. In FIG. 32, the hollow needle 942 has not yet contacted the sealing element 948, which remains solid and intact. In FIG. 33, however, engagement of the fluid reservoir 940 with the reservoir port receptacle 950 causes the sharp tip 944 to pierce the sealing element 948 such that the end of the hollow needle 942 resides within the outlet conduit 952. Accordingly, fluid communication is established from the fluid chamber 954 of the fluid reservoir 940 to the outlet conduit 952, via the hollow needle 942. In the state depicted in FIG. 33, the sealing element 948 forms a seal around the exterior surface of the hollow needle 942 to inhibit fluid leakage from the outlet conduit 952.

FIGS. 34-39 relate to a third embodiment of a needled fluid reservoir 960 that is suitable for use with a compatible fluid infusion device. The fluid reservoir 960 and the related features of the fluid infusion device are similar in many respects to that described above for the fluid reservoir 900. Accordingly, for the sake of brevity and clarity, the following description referring to FIGS. 34-39 is abbreviated in nature.

Figure 35:
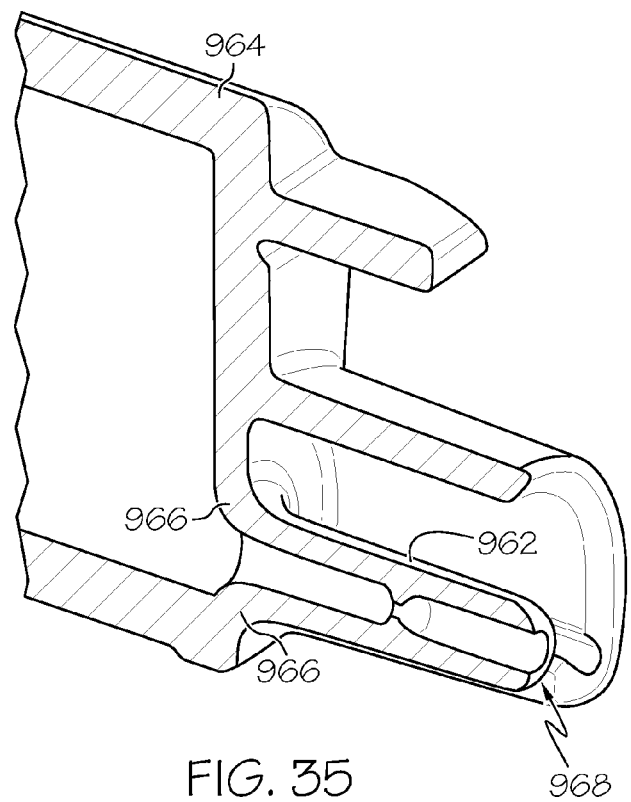
FIG. 35 is a cross-sectional view of a portion of the fluid reservoir, as viewed from the perspective of line 35-35 in FIG. 34.

The fluid reservoir 960 is very similar to the fluid reservoir 900, except for its use of an integrated hollow needle 962 rather than a physically distinct and separate needle component. In this regard, the hollow needle 962 is integrated and contiguous with the main body section 964 of the fluid reservoir 960. In certain embodiments, the hollow needle 962 and the main body section 964 are molded together from the same material (e.g., a plastic material) to create a unitary single component. The integrated nature of the hollow needle 962 is depicted in FIG. 35, which shows how the base 966 of the hollow needle 962 blends with (and is continuous with) the main body section 964. Although not always required, the illustrated embodiment of the hollow needle 962 terminates at a rounded, blunt tip 968. Alternatively, a pointed, angled, or sharp tip could be utilized.

Figure 36:
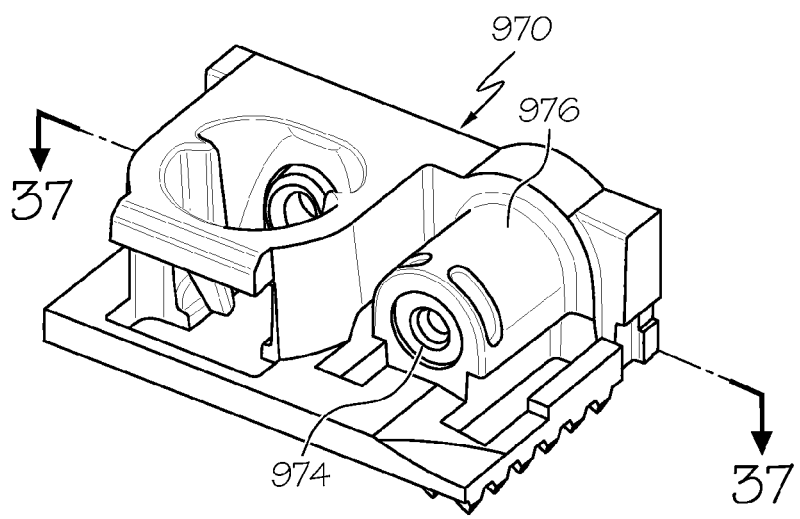
FIG. 36 is a perspective view of a section of a fluid infusion device, including a reservoir port receptacle suitable for engagement with the fluid reservoir shown in FIG. 34.
Figure 37:
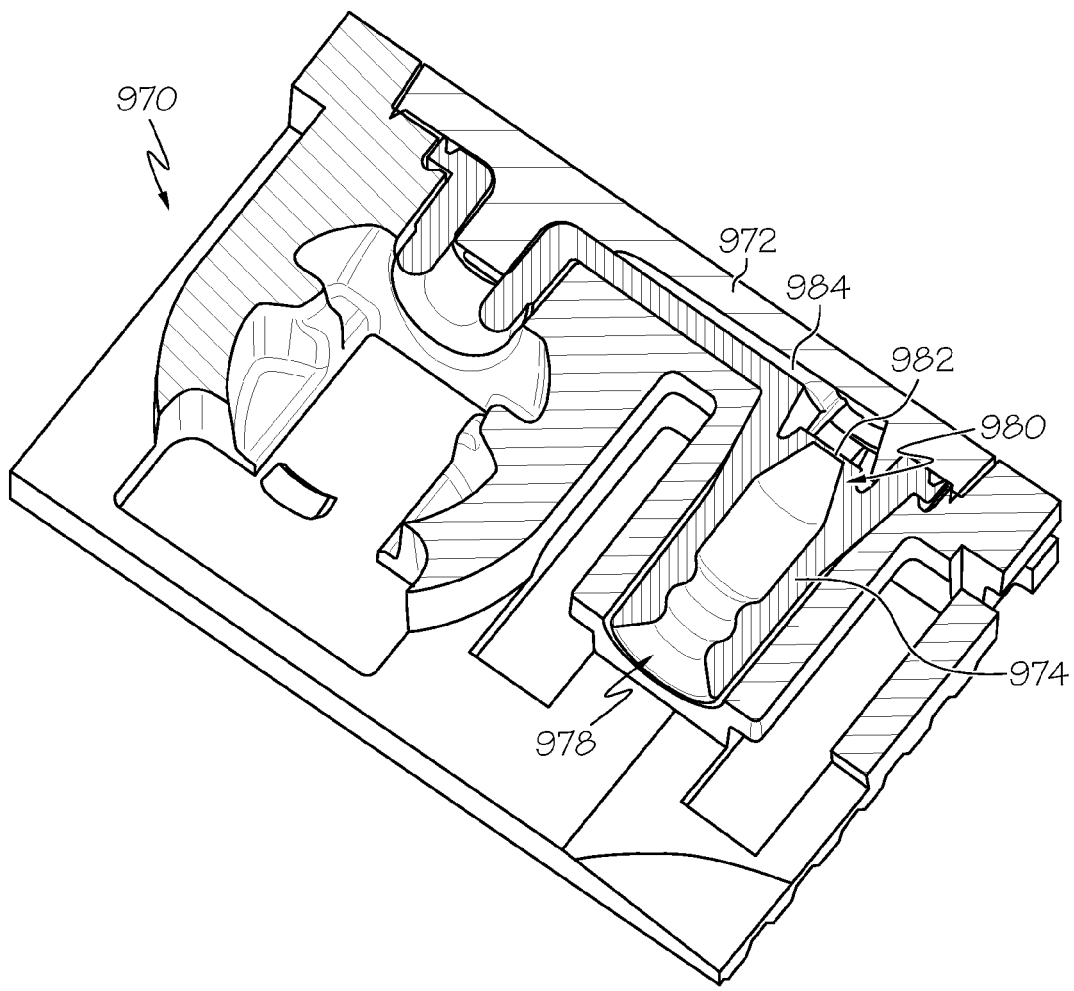
FIG. 37 is a cross-sectional view of the section of the fluid infusion device, as viewed from the perspective of line 37-37 in FIG. 36.

FIG. 36 depicts a section 970 of the fluid infusion device; the section 970 may represent a portion of the base plate (as described above). The section 970 houses a sealing and conduit component 972, which has the general characteristics and functionality described above for the previous two embodiments. The sealing and conduit component 972 includes or cooperates with a sealing element 974, which is accessible via a reservoir port receptacle 976. Notably, the sealing element 974 has an unsealed (open) inlet end 978 that is sized, shaped, and otherwise configured to receive the hollow needle 962. Moreover, the illustrated embodiment of the sealing element 974 has an outlet end 980 that is downstream from the inlet end 978. The outlet end 980 includes, cooperates with, or defines a pressure valve 982 that actuates in response to a fluid delivery action of the fluid infusion device, to accommodate flow of the medication fluid from the hollow needle to an outlet conduit 984. Consequently, even though the inlet end 978 of the sealing element 974 is open and exposed, the outlet conduit 984 is protected by the pressure valve 982 when the fluid reservoir 960 is removed from the reservoir port receptacle 976.

Figure 38:
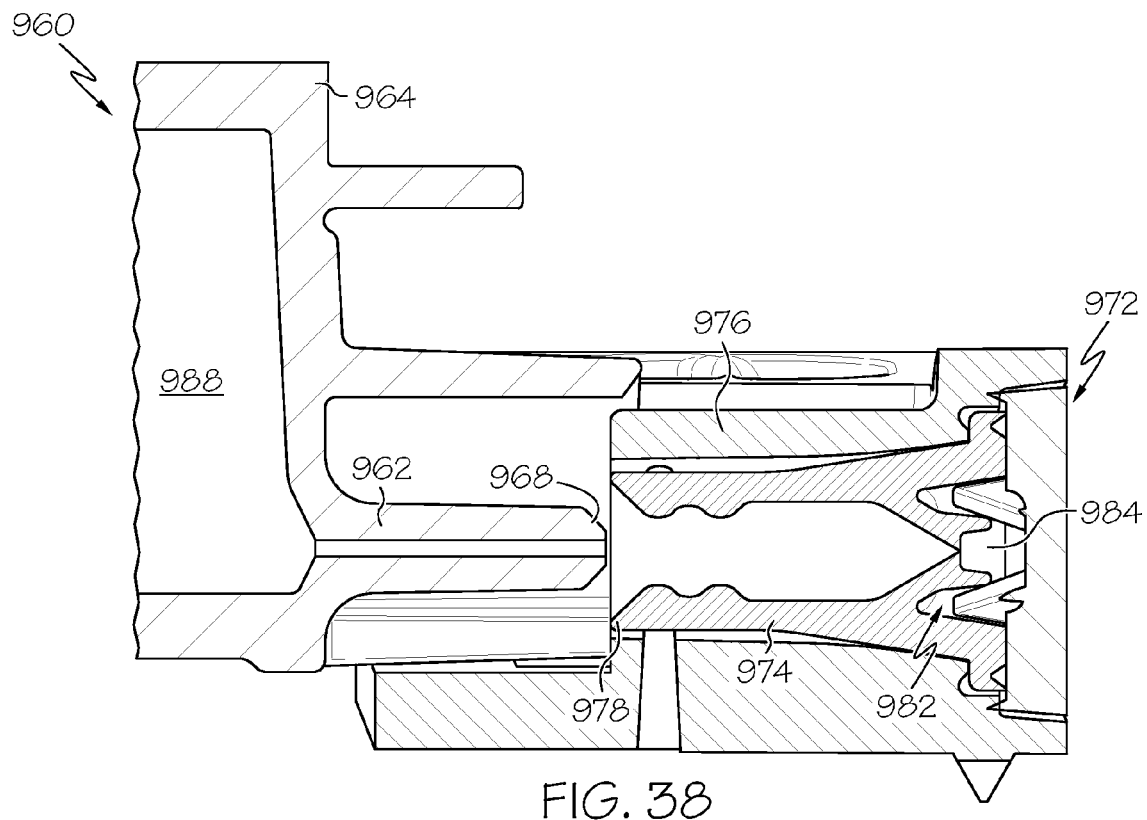
FIG. 38 is a cross-sectional and partially phantom view that illustrates the fluid reservoir (shown in FIG. 34) before engagement with the section of the fluid infusion device (shown in FIG. 36)
Figure 39:
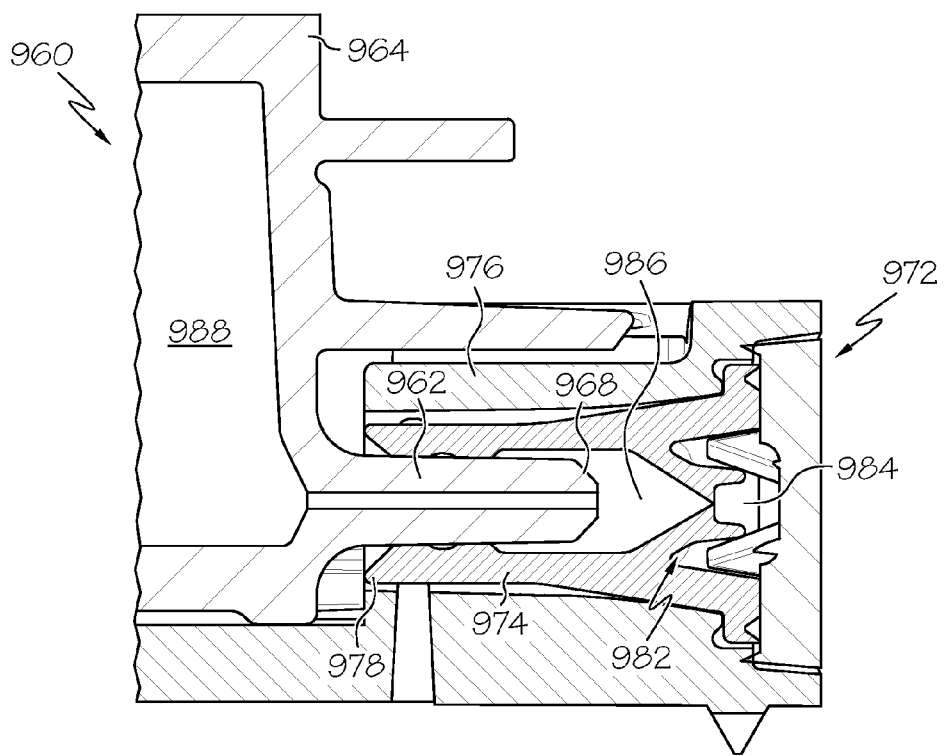
FIG. 39 is a cross-sectional and partially phantom view that illustrates the fluid reservoir (shown in FIG. 34) after engagement with the section of the fluid infusion device (shown in FIG. 36).

FIG. 38 is a cross-sectional and partially phantom view that illustrates the fluid reservoir 960 before engagement with the reservoir port receptacle 976, and FIG. 39 is a cross-sectional and partially phantom view that illustrates the fluid reservoir 960 after engagement with the reservoir port receptacle 976. In FIG. 38, the hollow needle 962 has not yet entered the sealing element 974. In FIG. 39, however, engagement of the fluid reservoir 960 with the reservoir port receptacle 976 urges the hollow needle 962 into the inlet end 978 of the sealing element 974 such that the end of the hollow needle 962 resides within a valve chamber 986 defined within the sealing element 974. Accordingly, fluid communication is established from the fluid chamber 988 of the fluid reservoir 960 to the valve chamber 986, via the hollow needle 962. In the state depicted in FIG. 39, the sealing element 974 forms a seal around the exterior surface of the hollow needle 962 to inhibit fluid leakage from the valve chamber 986.

FIG. 39 depicts the pressure valve 982 in a closed state, which is indicative of a lack of sufficient fluid pressure within the valve chamber 986. In contrast, when the plunger (not shown) of the fluid reservoir 960 is activated for a fluid delivery pulse, cycle, or action, the pressure valve 982 actuates and opens to accommodate flow of the medication fluid from the hollow needle 962 and through the pressure valve 982, by way of the valve chamber 986. The medication fluid is also urged through the outlet conduit 984, which may lead to a cannula that provides the medication fluid to the body of the patient.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A sealing assembly for a fluid infusion device, the sealing assembly comprising:
    a durable housing that receives and mates with a removable fluid reservoir having a fluid delivery port extending from the fluid reservoir and having a funnel-shaped interior defined therein, wherein the durable housing houses the removable fluid reservoir and retains the removable fluid reservoir in a particular position and orientation;
    a base plate having an adhesive layer of material to adhere the base plate to skin of a patient, and having a coupling structure to removably couple the base plate to the durable housing of the fluid infusion device;
    a reservoir port receptacle integrally formed with the base plate to receive and engage the fluid delivery port of the fluid reservoir in the particular position and orientation when the durable housing is coupled to the base plate, wherein the fluid delivery port of the fluid reservoir resides within the reservoir port receptacle when the durable housing is coupled to the base plate;
    a hollow fluid delivery needle coupled to the base plate and extending within the reservoir port receptacle to provide a fluid flow path from the fluid reservoir to a user of the fluid infusion device when the durable housing is coupled to the base plate; and a sealing element coupled to the base plate and overlying at least a portion of the hollow fluid delivery needle, the sealing element comprising:
  a base section;
  a tip section extending from the base section, the tip section shaped to enter and seal with the funnel-shaped interior of the fluid delivery port when the durable housing is coupled to the base plate;
  a retractable body section between the base section and the tip section;
  a needle cavity formed in the retractable body section and continuing through the base section to define a needle opening in the base section, the needle cavity sized to receive the hollow fluid delivery needle; and
  a self-sealing slit formed in the tip section to accommodate the hollow fluid delivery needle when the sealing element is in a retracted position caused by coupling of the durable housing with the base plate.

2. The sealing assembly of claim 1, wherein the sealing element further comprises a guide channel formed in the tip section and communicating with the needle cavity and the self-sealing slit, wherein the guide channel leads a tip of the hollow fluid delivery needle into the self-sealing slit during retraction of the sealing element caused by coupling of the durable housing with the base plate.

3. The sealing assembly of claim 1, wherein:
  the needle cavity defines internal relief features of the retractable body section;
  the internal relief features facilitate refraction of the sealing element over the hollow fluid delivery needle in response to a longitudinal force applied to the tip section by the fluid delivery port of the fluid reservoir, the longitudinal force caused by coupling of the durable housing with the base plate; and
  the internal relief features cause the sealing element to extend over and cover the hollow fluid delivery needle in response to removal of the longitudinal force.

4. The sealing assembly of claim 3, wherein the internal relief features comprise an accordion structure within the needle cavity.

5. The sealing assembly of claim 3, wherein the internal relief features comprise a plurality of internal annular channels within the needle cavity.

6. The sealing assembly of claim 3, wherein the internal relief features comprise a plurality of internal annular ridges within the needle cavity.

7. The sealing assembly of claim 3, wherein the internal relief features comprise a plurality of bottleneck structures within the needle cavity.

8. The sealing assembly of claim 1, wherein:
  the sealing element has a nominal state and a refracted state caused by coupling of the durable housing with the base plate;
  when in the nominal state, a tip of the hollow fluid delivery needle resides within the needle cavity, and the self-sealing slit forms a fluid seal to inhibit fluid ingress into the needle cavity; and
  when in the retracted state, an end section of the hollow fluid delivery needle resides in the self-sealing slit, and the tip of the hollow fluid delivery needle extends from the tip section of the sealing element.

9. The sealing assembly of claim 8, wherein:
  the retractable body section expands when the sealing element is retracting; and
  the retractable body section forms a fluid seal with the funnel-shaped interior of the fluid delivery port when the sealing element is in the retracted state.

10. The sealing assembly of claim 1, further comprising a circumferential compression element coupled around the tip section to impart an inward biasing force to the self-sealing slit.

11. The sealing assembly of claim 10, wherein the circumferential compression element comprises a rigid ring.

12. The sealing assembly of claim 10, wherein the circumferential compression element comprises a resilient band.

13. A sealing assembly for a fluid infusion device, the sealing assembly comprising:
  a durable housing that receives and mates with a removable fluid reservoir having a fluid delivery port extending from the fluid reservoir and having a funnel-shaped interior defined therein, wherein the durable housing houses the removable fluid reservoir and retains the removable fluid reservoir in a particular position and orientation;
  a base plate having an adhesive layer of material to adhere the base plate to skin of a patient, and having a coupling structure to removably couple the base plate to the durable housing of the fluid infusion device;
  a reservoir port receptacle integrally formed with the base plate to receive and engage the fluid delivery port of the fluid reservoir in the particular position and orientation when the durable housing is coupled to the base plate, wherein the fluid delivery port of the fluid reservoir resides within the reservoir port receptacle when the durable housing is coupled to the base plate;
  a hollow fluid delivery needle coupled to the base plate and extending within the reservoir port receptacle to provide a fluid flow path from the fluid reservoir to a user of the fluid infusion device when the durable housing is coupled to the base plate; and
  a sealing element coupled to the base plate and overlying at least a portion of the hollow fluid delivery needle, the sealing element comprising:
    a base section;
    a tip section extending from the base section, the tip section shaped to enter and seal with the funnel-shaped interior of the fluid delivery port when the durable housing is coupled to the base plate;
    a retractable body section between the base section and the tip section; and
    a needle cavity formed in the retractable body section and continuing through the base section to define a needle opening in the base section, the needle cavity sized to receive the hollow fluid delivery needle, and the needle cavity defining internal relief features of the retractable body section; wherein:
  the internal relief features promote deformation of the sealing element and retraction of the sealing element over the hollow fluid delivery needle in response to a longitudinal force applied to the tip section of the sealing element by the funnel-shaped interior of the fluid delivery port, the longitudinal force caused by coupling of the durable housing with the base plate; and
  the internal relief features cause the sealing element to automatically extend over the hollow fluid delivery needle into a nominal state in response to removal of the longitudinal force.

14. The sealing assembly of claim 13, wherein the sealing element encloses the hollow fluid delivery needle when the sealing element is in the nominal state.

15. The sealing assembly of claim 13, wherein the sealing element further comprises a self-sealing slit formed in the tip section to accommodate the hollow fluid delivery needle when the sealing element is in a retracted state caused by coupling of the durable housing with the base plate.

16. The sealing assembly of claim 15, wherein the sealing element further comprises a guide channel formed in the tip section and communicating with the needle cavity and the self-sealing slit, wherein the guide channel leads a tip of the hollow fluid delivery needle into the self-sealing slit during retraction of the sealing element caused by coupling of the durable housing with the base plate.

17. The sealing assembly of claim 13, wherein the internal relief features comprise an accordion structure within the needle cavity.

18. The sealing assembly of claim 13, wherein the internal relief features comprise a plurality of internal annular channels within the needle cavity.

19. The sealing assembly of claim 13, wherein the internal relief features comprise a plurality of internal annular ridges within the needle cavity.

20. The sealing assembly of claim 13, wherein the internal relief features comprise a plurality of bottleneck structures within the needle cavity.

21. The sealing assembly of claim 13, wherein:
the retractable body section comprises an exterior surface;
the exterior surface moves outward when the sealing element is retracting; and
the exterior surface forms a fluid seal with the funnel-shaped interior of the fluid delivery port when the sealing element is retracted.

* * * * *